(12) United States Patent
Takagi et al.

(10) Patent No.: US 9,414,800 B2
(45) Date of Patent: Aug. 16, 2016

(54) X-RAY OUTPUT APPARATUS

(71) Applicant: Sony Corporation, Tokyo (JP)

(72) Inventors: Yoshinori Takagi, Kanagawa (JP);
Hiromi Yoshinari, Kanagawa (JP);
Hisakazu Shiraki, Kanagawa (JP); Yuki Sugie, Kanagawa (JP)

(73) Assignee: Sony Corporation, Tokyo (JP)

( * ) Notice: Subject to any disclaimer, the term of this patent is extended or adjusted under 35 U.S.C. 154(b) by 228 days.

(21) Appl. No.: 14/324,290

(22) Filed: Jul. 7, 2014

(65) Prior Publication Data

US 2015/0016592 A1   Jan. 15, 2015

(30) Foreign Application Priority Data

Jul. 12, 2013   (JP) .................. 2013-146772

(51) Int. Cl.
*H01J 35/14*   (2006.01)
*A61B 6/00*   (2006.01)
*A61B 6/08*   (2006.01)

(52) U.S. Cl.
CPC .................. *A61B 6/5241* (2013.01); *A61B 6/08* (2013.01); *A61B 6/4007* (2013.01)

(58) Field of Classification Search
CPC ............ A61B 6/032; A61B 6/06; A61B 6/08; A61B 6/4007; A61B 6/5241; A61B 6/484; G01N 23/046; G01N 23/04; G01N 2223/401; G01T 1/295; H01J 35/065; H01J 2235/068; H01J 2235/062; H01J 35/14
USPC .......................... 378/147, 149, 150
See application file for complete search history.

(56) References Cited

U.S. PATENT DOCUMENTS

| | | | |
|---|---|---|---|
| 8,509,387 B2* | 8/2013 | Tsujii | A61B 6/06 378/122 |
| 2002/0075990 A1* | 6/2002 | Lanza | G01T 1/295 378/2 |
| 2008/0247504 A1* | 10/2008 | Edic | A61B 6/032 378/9 |

FOREIGN PATENT DOCUMENTS

JP   2009-025296 A   2/2009

* cited by examiner

*Primary Examiner* — Hoon Song
(74) *Attorney, Agent, or Firm* — Wolf, Greenfield & Sacks, P.C.

(57) ABSTRACT

There is provided a device including an X-ray output apparatus including an X-ray output section including a plurality of X-ray sources and outputting parallel X-ray beams, a shield section capable of changing a position which blocks the output parallel X-ray beams and permeate the parallel X-rays beams, and a control section controlling an output of the parallel X-ray beams at the X-ray output section and the position which permeates the parallel X-ray beams at a shield section.

14 Claims, 13 Drawing Sheets

A

B

C1

C2

X-RAY OUTPUT APPARATUS

CROSS REFERENCE TO RELATED APPLICATIONS

This application claims the benefit of Japanese Priority Patent Application JP 2013-146772 filed Jul. 12, 2013, the entire contents of which are incorporated herein by reference.

BACKGROUND

The present disclosure relates to an X-ray output apparatus.

For example, a CT (Computed Technology) apparatus (or a CT system, hereinafter similarly applied) utilizing X-rays output from a radiation source, and an apparatus (or system, hereinafter similarly applied) having a tomosynthesis function utilizing X-rays are widely used, for example, in a medical field.

A technology assuming parallel beam X-rays which output from an X-ray source is developed. The technology which produces tomosynthesis images by synthesizing a plurality of projected images which are obtained by making parallel X-rays be incident on a subject a plurality of times at different angles is described in JP 2009-25296A.

SUMMARY

X-rays include a property of being spread with the increase of a distance between an X-ray source outputting X-rays and a subject or a detector detecting the X-rays. Accordingly, when an irradiation area of X-rays is not restricted, the X-rays outputting from the X-ray source toward a specified position of the subject (for example, a region which is a subject of X-ray inspection) are irradiated on other positions than the specified position of the subject so that the subject is exposed to superfluous radiation with higher possibilities.

A means of preventing the occurrence of the above superfluous exposure to the subject includes the ingenious design of a collimator as shown, for example, in Patent Literature 1 for outputting the parallel X-ray beams so as to suppress the X-ray spread.

However, even if the X-ray spread is suppressed by outputting the parallel X-rays as described above, it is difficult to achieve the elimination of the X-ray spread. Therefore, even if the X-ray spread is suppressed by the ingenious design of the collimator as in above Patent Literature 1, for example, the sufficient reduction of the superfluous radiation exposure to the subject is not attained all the time.

Another means of preventing the above occurrence of proving the superfluous radiation exposure to the subject is supposed to bring an X-ray source close to a subject or a detector detecting X-rays. However, since the temperature of the X-ray source increases considerably at the X-ray output, it is difficult to decrease the distance between the X-ray source and the subject or the detector detecting the X-rays such that the influence of the X-ray spread is ignored.

The present disclosure proposes a novel and improved X-ray output apparatus which enables the reduction of superfluous radiation exposure given to a subject.

In accordance with the present disclosure, an X-ray output apparatus is provided which includes an X-ray output section including a plurality of X-ray sources and outputting parallel X-ray beams, a shield section capable of changing a position which blocks the output parallel X-ray beams and permeate the above parallel X-rays beams, and a control section controlling an output of the parallel X-ray beams at the X-ray output section and the position which permeates the parallel X-ray beams at the shield section, wherein the shield section includes a permeation aperture through which the parallel X-ray beams permeate, and a shield which blocks the parallel X-ray beams at a portion other than the permeation aperture, the control section controls, in a time-sharing manner, a position through which the parallel X-ray beams permeate in the shield section by moving the shield included in the shield section, a shape of the permeation aperture at a specified stage among shapes of the permeation aperture included in the shield section which permeates the parallel X-ray beams among respective stages of the time sharing is different from a shape of another stage, and the control section controls the position of the shield section which permeates the parallel X-ray beams such that an X-ray image based on each of the parallel X-ray beams at the respective stages in the time sharing manner which permeate the shield section includes no region overlapping with the other X-ray images.

According to the present disclosure, the superfluous radiation exposure to the subject can be reduced.

DETAILED DESCRIPTION OF THE EMBODIMENT(S)

Figure 1:
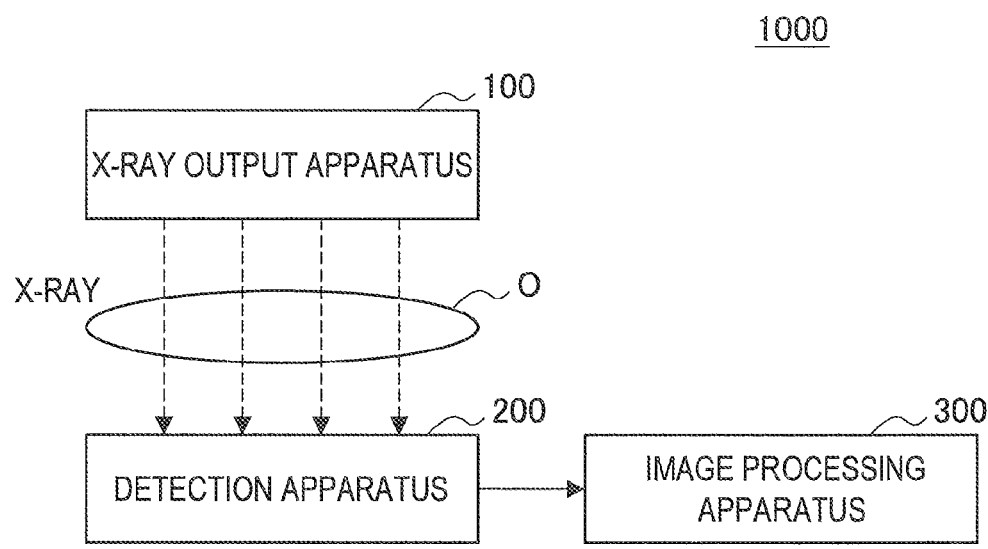
FIG. 1 is an illustration showing one example of the configuration of an X-ray inspection system in accordance with the present embodiment including an X-ray output apparatus in accordance with the present embodiment.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, the description will be performed in accordance with the order specified below.

1. Method of reducing radiation exposure in accordance with the present embodiment.
2. X-ray output apparatus in accordance with the present embodiment.
3. Program in accordance with the present embodiment.

(Method of Reducing Radiation Exposure in Accordance with the Present Embodiment)

A method of reducing radiation exposure in accordance with the present embodiment will be described while the configuration of an X-ray output apparatus in accordance with the present embodiment will be appropriately described. Hereinafter, the method of reducing the radiation exposure in accordance with the present embodiment will be described by using one example in which the above method is used in the X-ray inspection system in accordance with the present embodiment including the X-ray output apparatus in accordance with the present embodiment.

One example of configuration of X-ray inspection system in accordance with the present embodiment.

FIG. 1 is an illustration showing one example of the configuration of an X-ray inspection system 1000 in accordance with the present embodiment including an X-ray output apparatus 100 in accordance with the present embodiment. The X-ray inspection system 1000 includes, for example, the X-ray output apparatus 100, an inspection apparatus 200 and an image processing apparatus 300. In the X-ray inspection system 1000, the X-ray outputting from the X-ray output apparatus 100 and permeating interior of a subject "O" is inspected in the inspection apparatus 200 for inspecting the subject "O".

The X-ray output apparatus 100 outputs parallel X-ray beams. One example of the configuration of the X-ray output apparatus 100 will be described later.

The detection apparatus 200 includes, for example, a detection section (not shown) having a detector for detecting the X-rays, and produces X-ray detection data. Herein, the detector included in the detection apparatus includes, for example, FPD (Flat Panel Detector) and a photodiode. The X-ray detection data in accordance with the present embodiment are, for example, those exhibiting the detection strength of the X-ray having permeated the subject, which is detected by the detector.

The detection apparatus 200 may include, for example, a processing section (not shown) formed by MPU (Micro Processing Unit) and various processing circuits, ROM (Read Only Memory, not shown), RAM (Random Access Memory, not shown) and a communication section (not shown).

The processing section (not shown) included by the detection apparatus 200 converts the produced X-ray detection data into projection data (two-dimensional projection data), for example, by two-dimensionally projecting the above data as X-ray projection images. The processing section (not shown) included by the detection apparatus 200 converts the X-ray detection data into the projection data, for example, by the Radon transform. The detection apparatus 200 may not convert, for example, the X-ray detection data into the projection data. In case of the non-conversion of the X-ray detection data into the projection data, the X-ray detection data are transmitted to an external device via the communication section (not shown) and an external communication device.

The ROM (not shown) included by the detection apparatus 200 stores a program used by the processing section (not shown) included by the detection apparatus 200 and control data such as operation parameters. The ROM (not shown) included by the detection apparatus 200 temporarily stores a program implemented by the processing section (not shown) included by the detection apparatus 200.

The communication section (not shown) included by the detection apparatus 200 is a communication means included by the detection apparatus 200, and possesses a role of performing the communication by wired or wireless with an external device such as an image processing device 300.

The communication section (not shown) included by the detection apparatus 200 includes, for example, a communication antenna and an RF (Radio Frequency) circuit (wireless communication), an IEEE 802.15.1 port and a transmitting and receiving circuit (wireless communication), and an IFFF802.11b port and a transmitting and receiving circuit (wireless communication), or LAN (Local Area Network) terminal and a transmitting and receiving circuit (wired communication). The communication section (not shown) included by the detection apparatus 200 includes, for example, a configuration corresponding to any standard capable of performing the communication such as a USB (Universal Serial Bus) terminal and a transmitting and receiving circuit, and any configuration communicable with an external device via a network. A network in accordance with the present embodiment includes, for example, a wired network such as LAN and WAN (Wide Area Network), a wireless network such as WLAN (Wireless Local Area Network) and WWAN (Wireless Wide Area Network), or an internet using communication protocol such as TCP/IP (Transmission Control Protocol/Internet Protocol).

The image processing apparatus 300 processes, for example, the X-ray detection data or the projection data transmitted from the detection apparatus 200. The image processing apparatus 300 includes, for example, a processing section (not shown) constituted by MPU and various processing circuits, ROM (not shown), RAM (not shown) and a communication section (not shown).

The processing section (not shown) included by the image processing apparatus 300 has a role of, for example, processing the X-ray detection data or the projection data transmitted from the detection apparatus 200.

The processing of the X-ray detection data or the projection data at the processing section (not shown) included by the image processing apparatus 300 includes, for example, a processing of constituting X-ray images based on the X-ray detection data by re-constituting three-dimensional data from the projection data which is converted from the X-ray detection data. In case of transmitting the projection data from the detection apparatus 200, the processing section (not shown) included by the image processing apparatus 300 processes the projection data received by the communication section (not shown) included by the image processing apparatus 300 or the external communication device. In case of transmitting the X-ray data from the detection apparatus 200, the processing section (not shown) included by the image processing apparatus 300 converts the X-ray detection data received by the communication section (not shown) included by the image processing apparatus 300 or the external communication device into the projection data, and processes the converted projection data.

The processing of the X-ray detection data or the projection data at the processing section (not shown) included by the image processing apparatus 300 is not restricted to the above. The processing of the X-ray detection data or the projection data at the processing section (not shown) included by the image processing apparatus 300 in accordance with the present disclosure includes, for example, a stitching processing (laminating processing) in which images are laminated for completing one image from a plurality of shooting results, an offset processing for correcting fluctuation of X-ray strength at an output of an X-ray source and a noise elimination processing for eliminating (or reducing) noises having fluctuation such as thermal noises and electric source noises.

Figure 2:
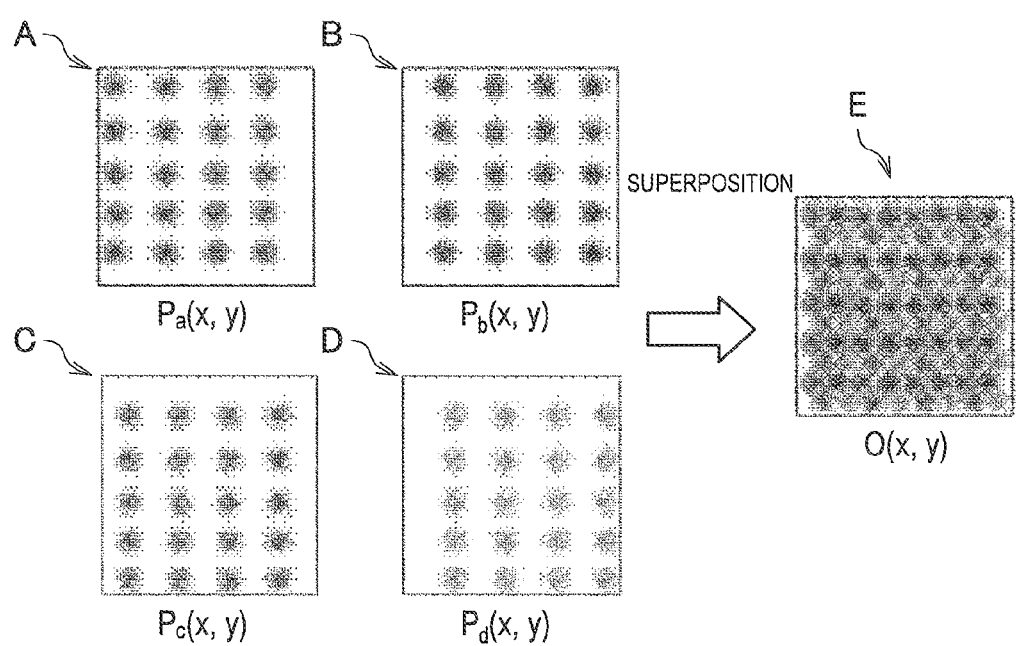
FIG. 2 is an illustration showing one example of the processing of an X-ray detection data in an image processing apparatus in accordance with the present embodiment.

FIG. 2 is an illustration showing one example of the processing of the X-ray detection data in the image processing apparatus 300 in accordance with the present embodiment, and shows one example of the stitching processing in accordance with the present embodiment in the processing section (not shown) included in the image processing apparatus 300. Herein, "A" to "D" shown in FIG. 2 show, for example, one example of a plurality of the X-ray images based on the X-ray detection data showing the respective detection results detected a plurality of times at the detection apparatus in a time-sharing manner. "E" shown in FIG. 2 show one example of the X-ray image (completed image) corresponding to the subject imaged by X-rays obtained by the stitching processing at the image processing apparatus 300.

The X-ray image (completed image) corresponding to the subject shown in "E" of FIG. 2 is obtained by superposing the plurality of the X-ray images based on the X-ray detection data showing the respective detection results detected the plurality of times in the time-sharing manner such shown in FIG. 2 as "A" to "D".

For example, as shown in FIG. 2, by superposing the plurality of the X-ray images based on the X-ray detection data showing the respective detection results detected the plurality of times in the time-sharing manner, the mutual influences among the X-rays output from the X-ray source such as those arranged in a side-by-side relation at an X-ray output section (described later) included in the X-ray output apparatus 100 can be reduced. For example, as shown in FIG. 2, by superposing the plurality of the X-ray images based on the X-ray detection data showing the respective detection results detected the plurality of times in the time-sharing manner, the influence of the unevenness of strength in the detected X-rays which may be generated by the diffusion of X-rays hereinafter described can be reduced, for example.

While, in FIG. 2, one example of obtaining the X-ray image (completed image) corresponding to the subject by superposing the four X-ray images "A" to "D" in FIG. 2 by the image processing apparatus 300, the number of the X-ray images to be superposed by the image processing apparatus 300 is not restricted to four. The image processing apparatus 300 can obtain the X-ray image corresponding to the subject by superposing two or more X-ray images based on the X-ray detection data showing the respective detection results detected in the time-sharing manner. More specifically, the image processing apparatus 300 can obtain the X-ray image corresponding to the subject by superposing a plurality of X-ray images based on the X-ray detection data showing the respective detection results detected in the time-sharing manner, under the conditions such as the number of imaging by the X-rays, the order of the imaging by the X-ray and a position where the X-rays are output at the X-ray output section (described later) included in the X-ray output apparatus 100.

For example, as shown by "E" of FIG. 2, the image processing apparatus 300 superposes the plurality of the X-ray images based on the X-ray detection data showing the respective detection results detected the plurality of times in the time-sharing manner such as "A" to "D" in FIG. 2 which include no overlapping region with the other X-ray images. For example, as shown by "E" of FIG. 2, the image processing apparatus 300 can obtain the X-ray image corresponding to the subject by superposing the plurality of the X-ray images based on the X-ray detection data showing the respective detection results detected the plurality of times in the time-sharing manner which include no overlapping region with the other X-ray images.

Figure 3:
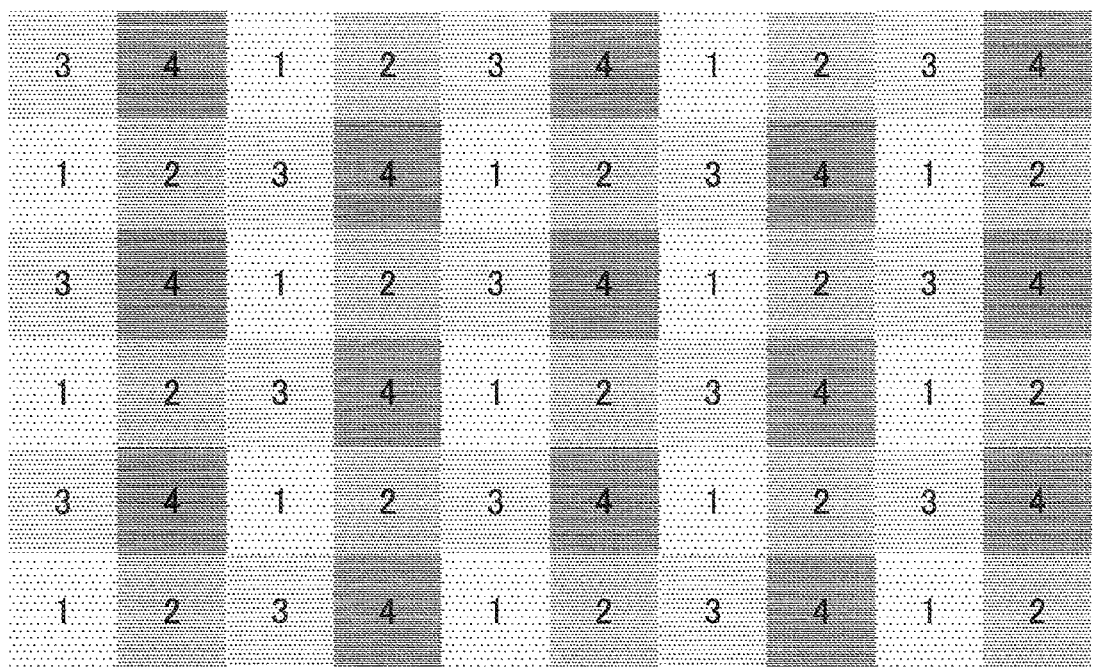
FIG. 3 is an illustration showing one example of the processing of an X-ray detection data in an image processing apparatus in accordance with the present embodiment.

FIG. 3 is an illustration showing one example of the processing of the X-ray detection data in the image processing apparatus 300 in accordance with the present embodiment, and shows one example of a plurality of X-ray images based on X-ray detection data used in the image processing apparatus 300. Herein, "1" to "4" shown in FIG. 3 refer to the detection order detected in the time-sharing manner, for example, in the image processing apparatus 300. That is, FIG. 3 shows an example of X-ray images by superposing the four X-ray images (from the X-ray image corresponding to the first detection result (the X-ray image corresponding to "1" in FIG. 3) to the X-ray image corresponding to the fourth detection result (the X-ray image corresponding to "4" in FIG. 3)) by means of the image processing apparatus 300 when the X-ray image corresponding to the subject is obtained, similar to the example shown in FIG. 2.

For example, as shown in FIG. 3, the X-ray images corresponding to "1" to "4" include no regions which overlap with the other X-ray images. Accordingly, the image processing apparatus 300 in accordance with the present embodiment can obtain the X-ray image corresponding to the subject by superposing the X-ray images corresponding to "1" to "4" shown in FIG. 3.

The plurality of the X-ray images based on the X-ray detection data which is possibly used by the image processing apparatus in the processing is not restricted to the X-ray images which are based on the X-ray detection data showing the respective detection results detected the plurality of times in the time-sharing manner and include no regions overlapping with the other X-ray images as shown in FIG. 3.

For example, the plurality of the X-ray images based on the X-ray detection data showing the respective detection results detected the plurality of times in the time-sharing manner in accordance with the present embodiment may include X-ray images having a region overlapping with each of the plurality of the X-ray images having no overlapping regions, in addition to the plurality of the X-ray images having no regions overlapping with the other X-ray images as shown in FIG. 3. For convenience of description, for example, the X-ray image based on the X-ray detection data showing the respective detection results detected the plurality of times in the time-sharing manner having no overlapping region with the other X-ray images is hereinafter referred to as "first X-ray image". For convenience of description, the X-ray image based on the X-ray detection data showing one of the respective detection results detected the plurality of times in the time-sharing manner having the overlapping region with each of a plurality of the first X-ray images is hereinafter referred to as "second X-ray image".

When a plurality of first X-ray images and a plurality of second X-ray images are included in the X-ray images based on the X-ray detection data showing the respective detection results detected the plurality of times in the time-sharing manner in accordance with the present embodiment, the image processing apparatus 300 corrects each of the plurality of the first X-ray images, for example, by using the second X-ray images as a standard. Then, the image processing apparatus in accordance with the present embodiment overlaps the corrected plurality of the first X-ray images from one another.

Figure 4:
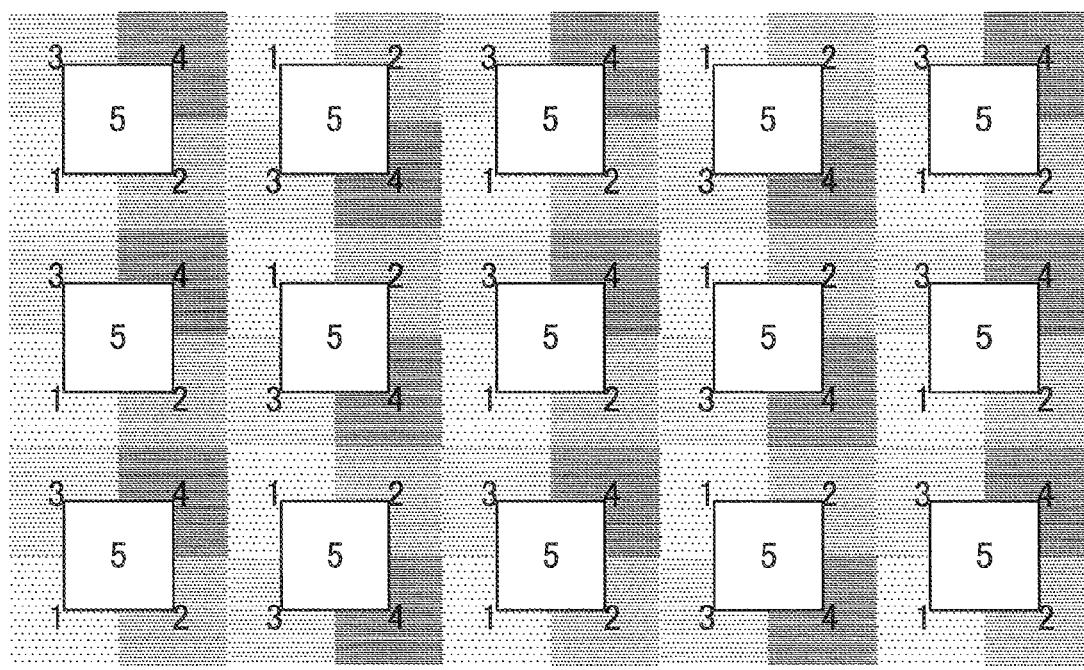
FIG. 4 is an illustration showing one example of the processing of X-ray detection data in an image processing apparatus in accordance with the present embodiment.
Figure 5:
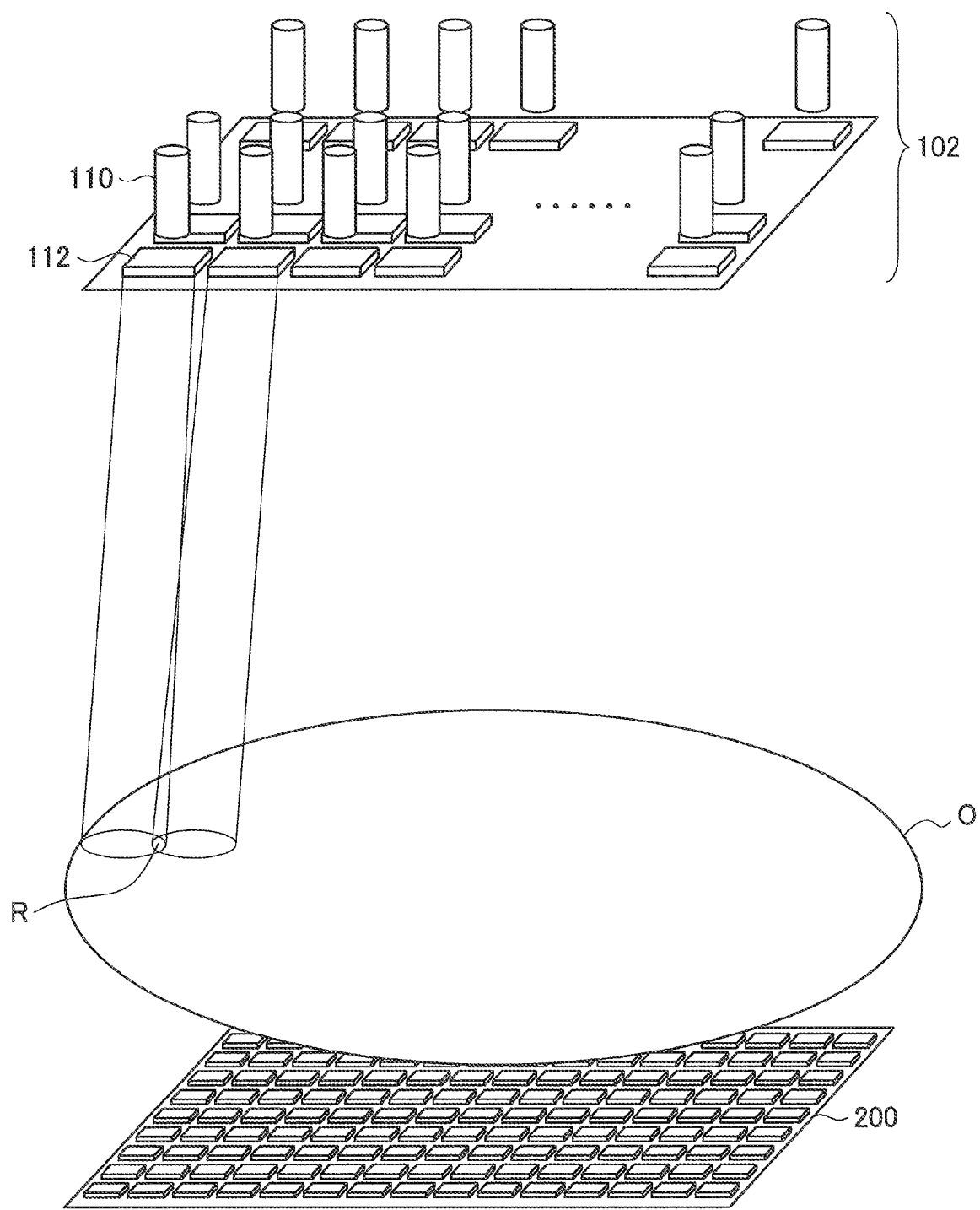
FIG. 5 is an illustration showing a method of reducing radiation exposure in accordance with the present embodiment.

FIG. 4 is an illustration describing one example of the processing of X-ray detection data in the image processing apparatus 300 in accordance with the present embodiment, and shows another example of the X-ray image based on the X-ray detection data which is used in the processing of the image processing apparatus 300. Herein, "1" to "5" shown in FIG. 5 shows the detection order detected, for example, in the detection apparatus 200. That is, in the example shown in FIG. 4, the X-ray images corresponding to the first detection results (the X-ray images corresponding to "1" in FIG. 4) to the X-ray images corresponding to the fourth detection results (the X-ray images corresponding to "4" in FIG. 4) corresponds to the first X-ray images. Also, in the example in FIG. 4, the X-ray images corresponding to the fifth detection results (the X-ray images corresponding to "5" in FIG. 4) corresponds to the second X-ray images.

While FIG. 4 shows the example in which dimensions between the X-ray images corresponding to the first detection results (the X-ray images corresponding to "1" in FIG. 4) to the X-ray images corresponding to the fourth detection results (the X-ray images corresponding to "4" in FIG. 4) corresponds to the first X-ray images and the X-ray images corresponding to the fifth detection results (the X-ray images corresponding to "5" in FIG. 4) are the same, a plurality of X-ray images based on the X-ray detection data usable in the processing of the imaged processing apparatus 300 are not restricted to the above. For example, the dimensions between the X-ray images corresponding to the first detection results (the X-ray images corresponding to "1" in FIG. 4) to the X-ray images corresponding to the fourth detection results (the X-ray images corresponding to "4" in FIG. 4) and the X-ray images corresponding to the fifth detection results (the X-ray images corresponding to "5" in FIG. 4) are different from each other. Also, for example, shapes between the X-ray images corresponding to the first detection results (the X-ray images corresponding to "1" in FIG. 4) to the X-ray images corresponding to the fourth detection results (the X-ray images corresponding to "4" in FIG. 4) and the X-ray images corresponding to the fifth detection results (the X-ray images corresponding to "5" in FIG. 4) may be the same or different from each other.

Each of the first X-ray images is that corresponding to each of the detection results in which the parallel X-ray beams are output from the X-ray output apparatus 100 in the time-sharing manner are detected in the time-sharing manner. Accordingly, there is a probability that an asymmetric nature (or an asymmetric system) in the unevenness of the X-ray strength may exist, for example, due to the difference in the degree of deterioration of each of a plurality of X-ray sources (hereinafter described) included in the X-ray output apparatus 100 and the difference in thermal influence by the X-ray output between the parallel X-ray beams output from the X-ray output apparatus 100 in the time-sharing manner.

When, as described above, there exists the asymmetric nature between the parallel X-ray beams output from the X-ray output apparatus 100 in the time-sharing manner, there is a risk that the X-ray images corresponding to the subject obtained by the superposition of the X-ray images corresponding to the respective results detected in the time-sharing manner are those including a bias due to the above asymmetric nature. The X-ray images including the bias due to the above asymmetric nature include, for example, the X-ray images having the bias along a horizontal direction as shown in FIG. 4.

When the above asymmetric nature between the parallel X-ray beams output from the X-ray output apparatus 100 in the time-sharing manner is corrected, the relations among the first X-ray images are equivalent. Accordingly, when the above asymmetric nature between the parallel X-ray beams output from the X-ray output apparatus 100 in the time-sharing manner is corrected, it is uncertain, in order to prevent the production of the X-ray images with the biases due to the above asymmetric nature, that the correction is conducted by using, as a standard, the first X-ray image corresponding to what number of the detection result.

On the other hand, the second X-ray images of the present embodiment are those having a region overlapped with each of the plurality of the first X-ray images. Accordingly, for example, when the image processing apparatus 300 corrects each of the plurality of the first X-ray images using the second X-ray image as a standard, it is possible to prevent that "the X-ray images corresponding to the subject obtained by the synthesize processing in accordance with the present embodiment become those including the biases due to the above asymmetric nature". The correction of each of the first X-ray images using the second X-ray images as a standard includes, for example, that of the X-ray strength of the first X-ray images (level correction).

Accordingly, when, for example, each of the plurality of the first X-ray images is corrected in the image processing apparatus 300 using the second X-ray image as a standard, the higher quality of the X-ray images corresponding to the subject obtained further by the superposition of the X-ray images corresponding to each of the detection results detected in the time-sharing manner.

The processing section (not shown) included in the image processing apparatus 300 enables to perform the processing, for example, shown in FIG. 2 to FIG. 4. The processing section (not shown) included in the image processing apparatus 300 can obtain the X-ray images corresponding to the subject by performing the processing, for example, shown in FIG. 2 to FIG. 4.

ROM (not shown) included in the image processing apparatus 300 stores control data such as programs and operational parameters used in the processing section (not shown) included in the image processing 300. RAM (not shown) included in the image processing apparatus 300 temporarily programs implemented by the processing section (not shown) included in the image processing 300.

A communication section (not shown) included in the image processing apparatus 300 is a communication means (not shown) included in the image processing 300, and has a role of perming communication by wired or wireless with an external device such as the detection apparatus 200 via a network (or directly)

The communication section (not shown) included by the detection apparatus 200 includes, for example, a communication antenna and an RF (Radio Frequency) circuit (wireless communication), an IEEE 802.15.1 port and a transmitting and receiving circuit, and an IFFF802.11b port and a transmitting and receiving circuit, or LAN terminal and a transmitting and receiving circuit (wired communication). The communication section (not shown) included by the detection apparatus 200 includes, for example, a configuration corresponding to any standard capable of performing the communication such as a USB terminal and a transmitting and receiving circuit, and any configuration capable of performing the communication with an external device via a network.

The X-ray inspection system 1000 in accordance with the present embodiment includes, for example, the configuration shown in FIG. 1. The X-ray detection system in accordance with the present embodiment is not restricted to the configuration shown in FIG. 1. For example, the X-ray detection system in accordance with the present embodiment may include a configuration without the image processing apparatus 300 shown in FIG. 1.

Summary of Method of Reducing Radiation Exposure in Accordance with Present Embodiment.

Then, summary of a method of reducing radiation exposure in accordance with the present embodiment will be described. Hereinafter, the method of reducing the radiation exposure in accordance with the present embodiment will be described taking an example in which the method of reducing radiation exposure in accordance with the present embodiment is applied to the X-ray output apparatus 100 constituting the X-ray inspection system 1000 shown in FIG. 1.

[2-1]

FIG. 5 is an illustration showing a method of reducing radiation exposure in accordance with the present embodiment. FIG. 5 shows an example of the X-ray output section 102 which is a constituent of the X-ray output apparatus 100, the detection apparatus 200 and the subject "O".

The X-ray output section 102 includes a plurality of X-ray sources 110 and outputs parallel X-ray beams. The output of the parallel X-ray beams at the X-ray output section 102 is controlled by, for example, a control section (described later) initiatively performing the processing of the method of reducing the radiation exposure in accordance with the present embodiment described later.

More specifically, the X-ray output section 102 which includes, for example, a plurality of X-ray sources 110 including X-ray tubes for generating X-rays and a plurality of collimators 112 for forming the parallel X-ray beams from the X-rays generated by the X-ray tubes outputs the parallel X-ray beams. FIG. 5 show an example in which the X-ray output section 102 is a planar radiation source including the X-ray sources 110 and collimators 112 disposed on a two-dimensional plane.

An example of the collimator 112 is a metal (for example, lead and iron) which is capable of blocking the X-rays and possesses a slit section capable of permeating the X-rays. The collimator 112 is not restricted to the metal which possesses the slit section capable of permeating the X-rays, and may be formed by any structure and material which includes the portions of blocking the X-rays and of permeating the X-rays for forming the parallel X-ray beams.

The configuration of the X-ray output section in accordance with the present embodiment is not restricted to that shown in FIG. 5. The X-ray output section in accordance with the present embodiment may include, for example, an X-ray source integrally constituted by the X-ray source 110 and the collimator 112 for outputting the parallel X-ray beams. While FIG. 5 shows the example of the X-ray source 110 and the collimator 112 in a one-to-one relation, the X-ray source 110 and the collimator 112 may not be in the one-to-one relation such as a configuration in which the plurality of the X-ray sources 110 and the collimator 112 correspond to each other.

The parallel X-ray beams output from the X-ray output section 102 are detected by the detector of the detection apparatus 200 after the permeation through the subject "O". Even if the X-ray spread is suppressed by outputting the parallel X-rays as described above, it is difficult to achieve the elimination of the X-ray spread. Therefore, as shown with "R" in FIG. 5, there is a probability of generating regions to which the parallel X-ray beams output from the plurality of the X-ray sources 110 are radiated in an overlapping manner (hereinafter referred to as "overlap radiation region").

Figure 6:
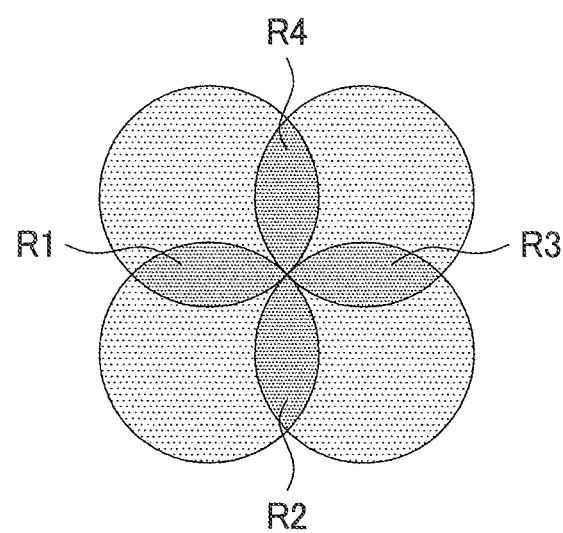
FIG. 6 is an illustration showing a method of reducing radiation exposure in accordance with the present embodiment.

FIG. 6 is an illustration showing the method of reducing the radiation exposure to in accordance with the present embodiment, and shows an example of the overlap radiation regions. FIG. 6 shows an example of the overlap radiation regions R1 to R4 which may be formed by the parallel X-ray beams output from four X-ray sources.

As shown by R1 to R4 in FIG. 6, the parallel X-ray beams output from the plurality of the X-ray sources are radiated on the overlap radiation regions. An amount of the radiation exposure in the overlap radiation regions R1 to R4 is larger than in other regions to which the X-rays are radiated. Accordingly, the radiation exposure to the subject in the overlap radiation regions R1 to R4 is "invalid radiation exposure" which corresponds to superfluous radiation exposure to the subject.

The X-ray output apparatus 100 further includes, in addition to the X-ray output section 102, a shield section having a variable position for blocking and permeating the output parallel X-ray beams. The shield section in accordance with the present embodiment includes one or more shields which include permeation apertures and block the parallel X-rays at portions other than the permeation apertures. An example of the shield included in the shield section in accordance with the present embodiment will be described later.

The X-ray output apparatus 100 implements to reduce the superfluous radiation exposure to the subject by means of eliminating the invalid radiation exposure as shown with R1 to R4 in FIG. 6 by controlling the positions of permeating and blocking the parallel X-ray beams in the shield sections in accordance with the present embodiment.

[2-2]

For example, as shown in FIG. 4, when the superposing processing of the first X-ray images is conducted in the image processing apparatus 300, there is a risk that the X-ray images corresponding to the subject obtained by the superposition of the X-ray images corresponding to the respective results detected in the time-sharing manner are those including the bias due to the asymmetric nature. Accordingly, when the superposing processing of the first X-ray images is conducted in the image processing apparatus 300, the high quality of the X-ray images corresponding to the subject obtained by the superposition of the X-ray images corresponding to each of the detection results detected in the time-sharing manner is not obtained all the time.

When, for example as shown in FIG. 4, the image processing apparatus 300 corrects each of the plurality of the first X-ray images, by using the second X-ray images as a standard, the higher quality of the X-ray images corresponding to the subject obtained by the further superposition of the X-ray images corresponding to each of the detection results detected in the time-sharing manner can be obtained.

However, the second X-ray images in accordance with the present embodiment are those which are based on the X-ray detection data showing one detection result among the detection results detected the plurality of times in the time-sharing manner and include the regions overlapped with each of the plurality of the first X-ray images. Accordingly, for example as shown in FIG. 4, the image processing apparatus 300 corrects each of the plurality of the first X-ray images by using the second X-ray images as a standard, an amount of the radiation exposure to the subject increases for obtaining the second X-ray images.

By controlling the positions in the shield sections in accordance with the present embodiment through which the parallel X-ray beams permeate in the time-sharing manner, the X-ray output apparatus 100 obtains the higher quality-X-ray images corresponding to the subject at the image processing apparatus 300 while the increase of the amount of the radiation exposure to the subject is prevented.

The X-ray output apparatus 100 controls, in the time-sharing manner, the positions in the shield sections in accordance with the present disclosure through which the parallel X-ray beams permeate by moving the shield included in the shield section in accordance with the present disclosure. When, for example, the shield included in the shield sections in accordance with the present disclosure includes a configuration in which a desired portion of the shied can be selectively made to a permeation aperture by means of a shuttering mechanism, the X-ray output apparatus 100 may control, in the time-sharing manner, the positions of the shield sections in accordance with the present disclosure through which the parallel X-ray beams permeate by, for example, changing the positions acting as the permeation apertures in the shield by means of the control of the shuttering mechanism. An example will be described in which the X-ray output apparatus 100 changes the positions of the shield sections in accordance with the present disclosure through which the parallel X-ray beams permeate in the time-sharing manner by moving the shield included in the shield section in accordance with the present disclosure.

In case of moving the shield included in the shield section 104, the X-ray output apparatus 100 stops the output of the parallel X-ray beams, for example, at the X-ray output section 102. Then, the X-ray output apparatus 100, for example, outputs the parallel X-ray beams to the X-ray output section 102 after the completion of the movement of the shield included in the shield section 104.

The processing of the output control of the parallel X-ray beams at the X-ray output section 102 of the X-ray output apparatus 100 is not restricted to the above. For example, in case of the output of the parallel X-ray beams to the X-ray output section 102, the X-ray output apparatus 100 may output, toward the X-ray output section 102, the parallel X-ray beams only to the positions corresponding to the positions of the shield section 104 through which the parallel X-ray beams permeate. For example, the X-ray output apparatus 100 outputs the parallel X-ray beams only to the positions corresponding to the positions of the shield section 104 through which the parallel X-ray beams permeate by controlling the output and the non-output of the parallel X-ray beams at the respective X-ray sources 110 included in the X-ray output section 102.

The control of the positions through which the parallel X-ray beams permeate in the shield section in accordance with the present disclosure in the time-sharing manner will be described. The X-ray output apparatus 100 controls the positions through which the parallel X-ray beams permeate in the shield section in accordance with the present disclosure such that the X-ray images based on each of the parallel X-ray beams at the respective stages in the time sharing and having permeated the shield section in accordance with the present disclosure does not include any region overlapping with other X-ray images. That is, at the respective stages in the time sharing, each of the X-ray images based on parallel X-ray beams having permeated the shield section in accordance with the present disclosure corresponds to the above first X-ray images in accordance with the present disclosure.

For the control in the time-sharing, the X-ray output apparatus 100 controls the positions through which the parallel X-ray beams permeate in the shield section in accordance with the present disclosure such that the shapes of the permeation apertures at the specified stages among those included in the shield section in accordance with the present disclosure for permeating the parallel X-lay beams are different from the shapes at the other stages.

The X-ray images based on the parallel X-ray beams having permeated the shield section in accordance with the present disclosure at the specified stage in accordance with the present disclosure of the above control in the time-sharing manner are a standard of correcting each of the X-ray images having permeated the shield section in accordance with the present disclosure at the other stages in accordance with the present disclosure of the above control in the time-sharing manner. For convenience for the description, the X-ray images based on the parallel X-ray beams having permeated the shield section in accordance with the present disclosure at the specified stage in accordance with the present disclosure of the above control in the time-sharing manner are hereinafter referred to as "third X-ray images". For convenience for the description, the X-ray images having permeated the shield section in accordance with the present disclosure at the other stages in accordance with the present disclosure of the above control in the time-sharing manner are hereinafter referred to as "fourth X-ray images".

That is, the third X-ray images (the X-ray images based on the parallel X-ray beams having permeated the shield section in accordance with the present disclosure at the specified stage in accordance with the present disclosure of the above control in the time-sharing manner) have the role of the second X-ray images in accordance with the present disclosure described above in addition to the role of the first X-ray images in accordance with the present disclosure described above.

When the X-ray output apparatus 100 performs the processing of the method of reducing the radiation exposure in accordance with the present disclosure described above, the image processing apparatus 300 corrects each of the plurality of the fourth X-ray images by using the third X-ray images as a standard, for example, similarly to the correction of each of the plurality of the first X-ray images by using the second X-ray images as a standard in FIG. 4. In the above case, for example, the image processing apparatus 300 superposes the third X-ray images with each of the corrected plurality of the fourth X-ray images.

Accordingly, when the X-ray output apparatus 100 performs the method of reducing the radiation exposure in accordance with the present embodiment as described above, the image processing apparatus 300 can produce the higher quality X-ray images corresponding to the subject obtained by the superposition of the X-ray images corresponding to each of the detection results detected in the time-sharing manner, for example, similarly to the processing described referring to FIG. 5.

When the X-ray output apparatus 100 performs the method of reducing the radiation exposure in accordance with the present embodiment as described above, the X-ray images (the third X-ray images and the fourth X-ray images) corresponding to each of the detection results detected in the time-sharing manner include no regions overlapping with the other X-ray images. Accordingly, when the X-ray output apparatus 100 performs the method of reducing the radiation exposure in accordance with the present embodiment as described above, an amount of the radiation exposure to the subject can be more reduced than, for example, the case of correcting each of the first X-ray images using the second X-ray images as a standard as shown in FIG. 4.

Accordingly, the X-ray output apparatus 100 can produce the higher quality X-ray images corresponding to the subject obtained by the superposition of the X-ray images corresponding to each of the detection results detected in the time-sharing manner, while the increase of the amount of the radiation exposure to the subject is prevented, by conducting the processing of the method of reducing the radiation exposure in accordance with the present embodiment.

Processing in Method of Reducing Radiation Exposure in Accordance with Present Embodiment Then, the processing in the method of reducing the radiation exposure in accordance with the present embodiment in the X-ray output apparatus in accordance with the present embodiment will be described. Hereinafter, the method of reducing the radiation-exposure in accordance with the present embodiment will be described taking an example in which the X-ray output apparatus in accordance with the present embodiment is the X-ray output apparatus 100 configuring the X-ray inspection system 1000 shown in FIG. 1.

Figure 7:
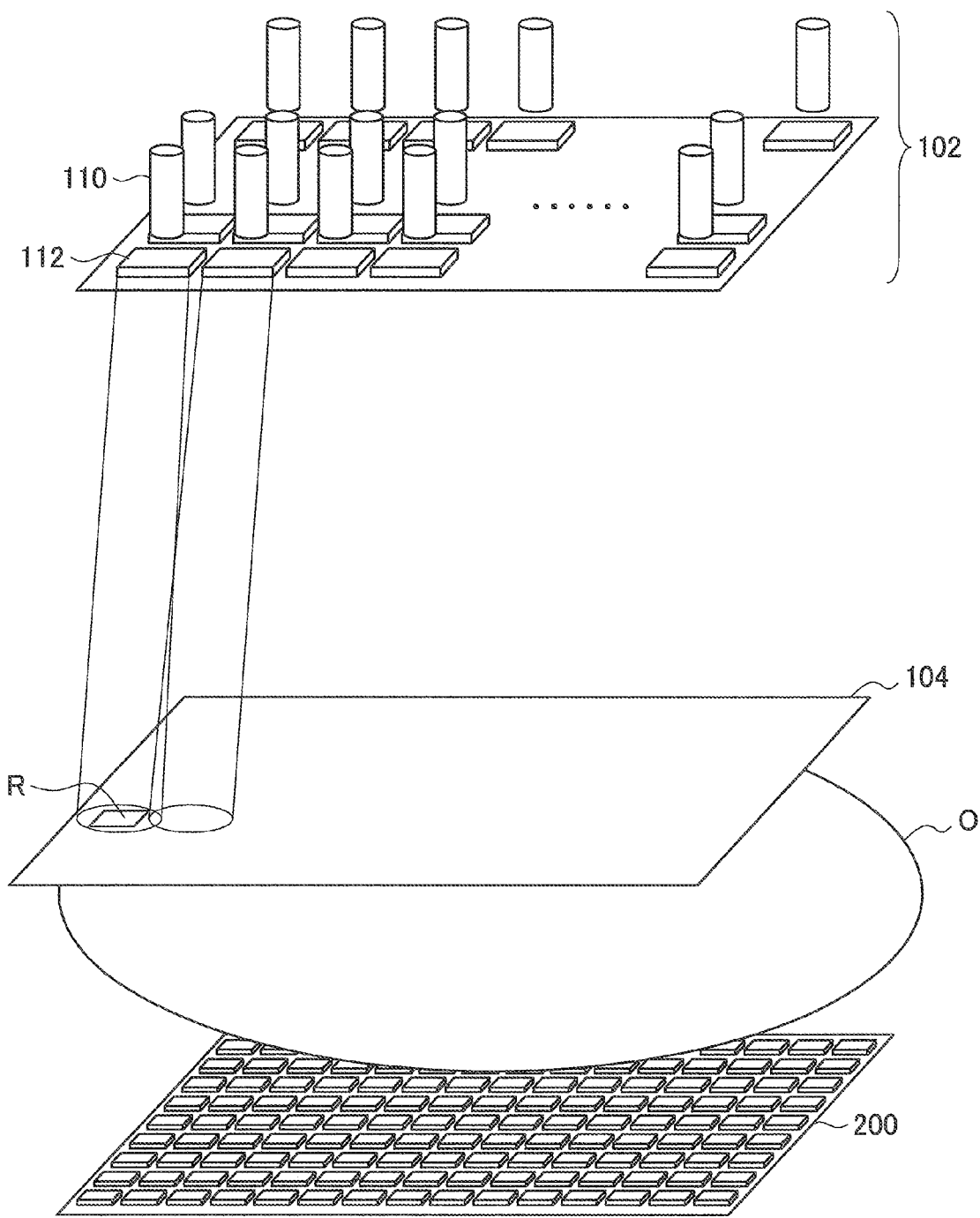
FIG. 7 is an illustration showing processing of a method of reducing radiation exposure in accordance with the present embodiment.

FIG. 7 is an illustration showing processing of the method of reducing the radiation exposure in accordance with the present embodiment. FIG. 7 shows an example of the X-ray output section 102 constituting part of the configuration of the X-ray output apparatus 100, the shield section 104, the detection apparatus 200 and the subject "O".

The shield section 104 blocks the output parallel X-ray beams. The position through which the parallel X-ray beams can permeate is variable in the shield section 104. The position through which the parallel X-ray beams permeate in the shield section 104 is controlled by, for example, a control section (described later) initiatively performing the processing of the method of reducing the radiation exposure in accordance with the present embodiment described later.

The shield section 104 includes the permeation aperture permeating the parallel X-ray beams, and includes the shield for blocking the parallel X-ray beams at the positions other than the permeation aperture. While an example in which the shield section 104 includes one shield in FIG. 7, the number of the shields included in the shield section 104 is not restricted to one. For example, the shield section 104 may include a plurality of the shields. An example of the shield included in the shield section 104 will be described later, Examples of the shield included in the shield section 104 include, for example, a metal plate including a metal which can block the X-rays such as lead and iron, and glass containing the above metal. The shield included in the shield section 104 may be constituted with any material which can block the X-rays.

"R" shown in FIG. 7 shows one example of the region corresponding to the position through which the parallel X-rays permeate. For example, the region "R" shown in FIG. 7 is formed by a permeation aperture included by one shield constituting the shield section 104, or a permeation aperture formed when a plurality of the shields constituting the shield section 104 are superposed. For convenience of description, for example, "the permeation aperture included by one shield constituting the shield section 104" and "the permeation aperture formed when the plurality of the shields constituting the shield section 104 are overlapped" may be collectively referred to simply as "permeation aperture" or "permeation aperture of shield section".

The X-ray output apparatus 100 controls the position such as the region "R" of FIG. 7 through which the parallel X-rays permeate in the shield position 104 in the time-sharing manner by changing the above position in the time-sharing manner by moving the shield included in the shield section.

More specifically, when the shield section 104 includes one shield, the X-ray output apparatus 100 changes, in the time-sharing manner, the position of the permeation aperture included in the shield by, for example, moving the shield. When the shield section 104 includes one shield, the shield includes the permeation apertures having a plurality of shapes. An example of the permeation apertures having the plurality of the shapes when the shield section 104 includes one shield is similar to that of the permeation aperture used in a case where the shield section 104 described later and including a plurality of the shields.

When the shield section 104 includes a plurality of the shields in which the shapes of the permeation apertures of every shield are different from one another, the X-ray output apparatus 100 controls the position through which the parallel X-rays permeate of the shield section 104 by using one of the shields among the plurality of the shields included in the shield section 104, for example, at the respective stages which controls the position through which the parallel X-rays permeate. The X-ray output apparatus 100 makes it possible to permeate the parallel X-ray beams output from the X-ray output section 102 through one of the shields by appropriately moving each of the shields included in the shield section 104. Or, the X-ray output apparatus 100 makes it not possible to permeate the parallel X-ray beams output from the X-ray output section 102 through another shield by appropriately moving each of the shields included in the shield section 104.

When the shield section includes a plurality of the shields in which every shield has a different shape of the included permeation aperture, the processing is not restricted to the above.

When the shield section 104 includes a plurality of the shields in which the shapes of the permeation apertures of every shield are different from one another, the X-ray output apparatus 100 can control the position through which the parallel X-rays permeate of the shield section 104 by the plurality of the shields among the plurality of the shields included in the shield section 104, for example, at the respective stages which controls the position through which the parallel X-rays permeate. The X-ray output apparatus 100 changes the position and the shape of the permeation aperture formed by the superposition of the plurality of the shields, for example, by changing a way of the superposition of the plurality of the shields included in the shield section 104.

For convenience of description, one example of the processing of the method of reducing the radiation exposure in accordance with the present disclosure will be described mainly taking an example in which the shield section 104 includes two shields one of which is a first shield including a permeation aperture and another of which is a second shield having a permeation aperture whose shape is different from that of the first shield (one example including a plurality of the shields).

As described above, the shield section 104 may include the configuration including one shield. When the shield section 104 includes the configuration including one shield, the shield includes, for example, both of the permeation aperture included in the first shield of the present embodiment and the permeation aperture included in the second shield of the present embodiment. The X-ray output apparatus 100 makes a situation similar to a case one of the shields including the first shield and the second shield of the present embodiment is used by moving one shield included in the X-ray output apparatus 100, and controls the position of the shield section 104 through which the parallel X-ray beams permeate.

Figure 8:
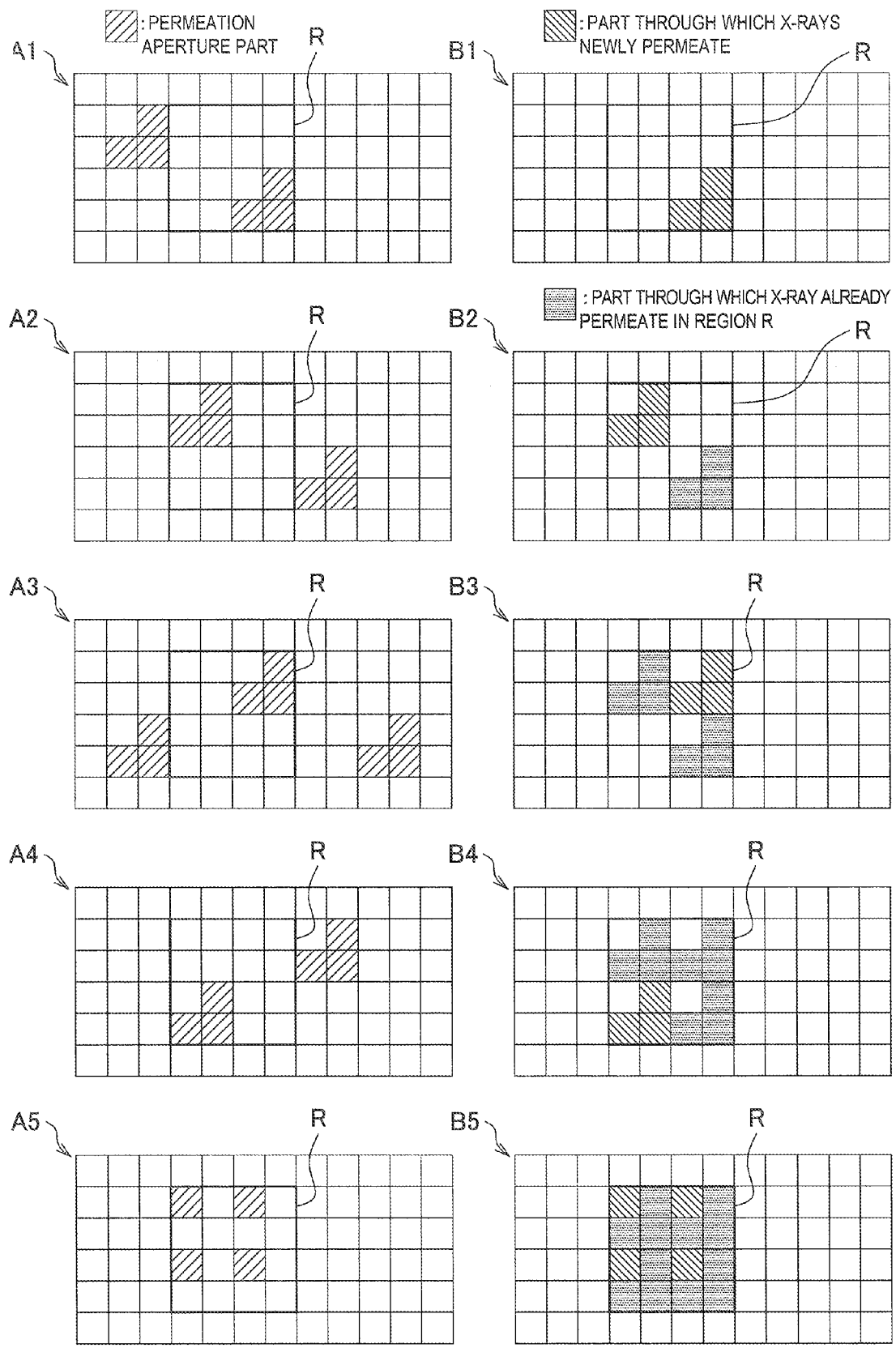
FIG. 8 is an illustration showing a first example of processing of a method of reducing radiation exposure in accordance with the present embodiment.

[3-1] First Example of Processing of Method of Reducing Radiation Exposure of Present Embodiment FIG. 8 is an illustration showing a first example of the processing of the method of reducing the radiation exposure of the present embodiment.

Herein, A1 to A5 shown in FIG. 8 show one example of the positions of the shield section 104 through which the parallel X-ray beams permeate in a chronological order from A1 to A5. That is, the example of FIG. 8 shows that the positions of the shield section 104 through which the parallel X-ray beams permeate are controlled in the time-sharing manner five times A1 to A5. As shown in the example of FIG. 8, when the positions of the shield section 104 through which the parallel X-ray beams permeate are controlled in the time-sharing manner, the detection apparatus 200 detects the X-rays at the respective stages A1 to A5 of FIG. 8.

FIG. 8 shows one example of the positions of the shield section 104 through which the parallel X-ray beams permeate when the shield section 104 includes the first shield having "permeation apertures with an asymmetric shape prepared by combining squares" shown as A1 to A4 in FIG. 8 and the second shield having "square-shaped permeation apertures" shown as A5 in FIG. 8. More specifically, A1 to A4 shown in FIG. 8 show one example in which the positions of the shield section 104 through which the parallel X-ray beams permeate are controlled by moving the first shield including the shield section 104 along a right-side direction in FIG. 8. A5 shown in FIG. 8 shows one example in which the position of the shield section 104 through which the parallel X-ray beams permeate is controlled by moving the second shield included in the shield section 104 to the position shown by A5 in FIG. 8.

The regions "R" shown in A1 to A5 of FIG. 8 show the same regions in the shield section 104. B1 to B5 shown in FIG. 8 show the states of the X-ray permeation in the regions R of the shield section 104, and each of B1 to B5 shown in FIG. 8 corresponds to the respective stages of A1 to A5 of FIG. 8.

The X-rays can permeate the entire region R in the shield section 104 without overlapping of the X-rays, for example, as shown by B5 in FIG. 8 by using, for example, "the permeation apertures with the asymmetric shape prepared by combining squares" shown as A1 to A4 in FIG. 8 and "the square-shaped permeation apertures" shown as A5 in FIG. 8.

The X-ray images based on the parallel X-ray beams permeating the shield section 104 at the stage shown with A5 of FIG. 8 include a region adjacent to each of the parallel X-ray beams permeating the shield section 104 at the stages shown with A1 to A4 of FIG. 8. Accordingly, the X-ray images based on the parallel X-ray beams permeating the shield section 104 at the stage shown with A5 of FIG. 8 can be a standard of correcting each of the X-ray images permeating the shield section 104 at the other stages (the stages A1 to A5 of FIG. 8) shown with A5 of FIG. 8. That is, the stage shown with A5 among the respective stages A1 to A5 in the time-sharing manner corresponds to the specified stage of the present embodiment, and the X-ray images based on the parallel X-ray beams permeating the shield section 104 at the stage shown with A5 of FIG. 8 correspond to the third X-ray images.

The specified stage of the present embodiment is not restricted to the last stage in the time-sharing manner. For example, the X-ray output apparatus 100 can establish any stage in the time-sharing manner as the specified stage of the present embodiment by moving the shield included in the shield section 104 for making a situation similar to the stage shown with A5 of FIG. 8.

For example, as shown in FIG. 8, the shape of the permeation apertures at the specified stage (the stage A5 in the example of FIG. 8) among the shapes of the permeation apertures included in the shield section 104 through which the parallel X-ray beams permeate at the respective stages in the time-sharing manner is different from the shapes at the other stages (the stages A1 to A4 in the example of FIG. 8).

The X-ray output apparatus 100 controls the positions of the shield section 104 through which the parallel X-ray beams permeate, for example, at the respective stages A1 to A4 of FIG. 8 by using the first shield between the said first shield having "the permeation apertures with the asymmetric shape prepared by combining the squares" shown with A5 of FIG. 8 and the second shield having "the square-shaped permeation apertures". The X-ray output apparatus 100 controls the position of the shield section 104 through which the parallel X-ray beams permeate at the stage A5 of FIG. 8 by using the second shield between the first shield having "the permeation apertures with the asymmetric shape prepared by combining the squares" and the second shield having "the square-shaped permeation apertures" as shown at A5 of FIG. 8, for example, at the stage A5 of FIG. 8.

The shapes of the permeation apertures included in the first shield of the present embodiment and those included in the second shield of the present embodiment are not restricted to "the permeation apertures with the asymmetric shape prepared by combining the squares" and "the square-shaped permeation apertures", respectively, as shown in FIG. 8.

For example, the shapes of the permeation apertures included in the first shield and the second shield of the present embodiment may be such that a shape of a permeation aperture formed by the superposition of the first shield and the second shield of the present embodiment becomes "the permeation apertures with the asymmetric shape prepared by combining the squares" or "the square-shaped permeation apertures" depending on a way of the superposition between the first shield and the second shield of the present embodiment.

Figure 9:
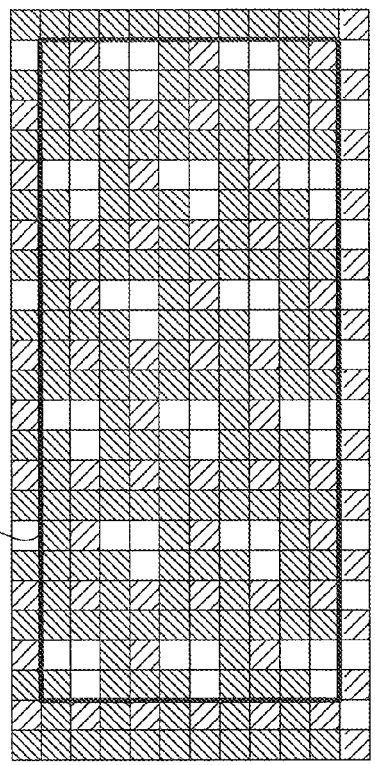
FIG. 9 is an illustration showing a first example of processing of a method of reducing radiation exposure in accordance with the present embodiment.
Figure 9:
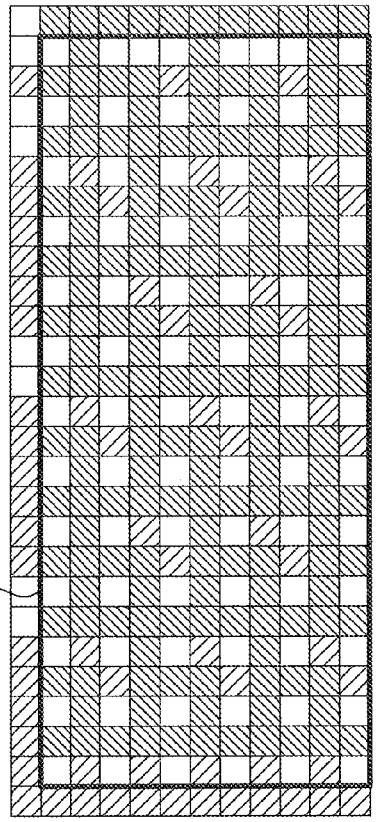
Figure 9:
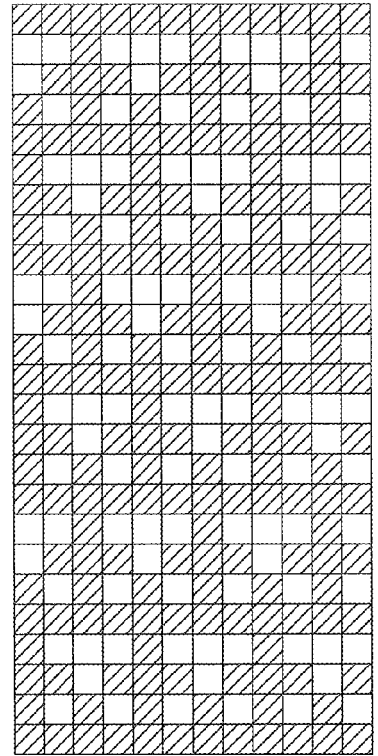
Figure 9:
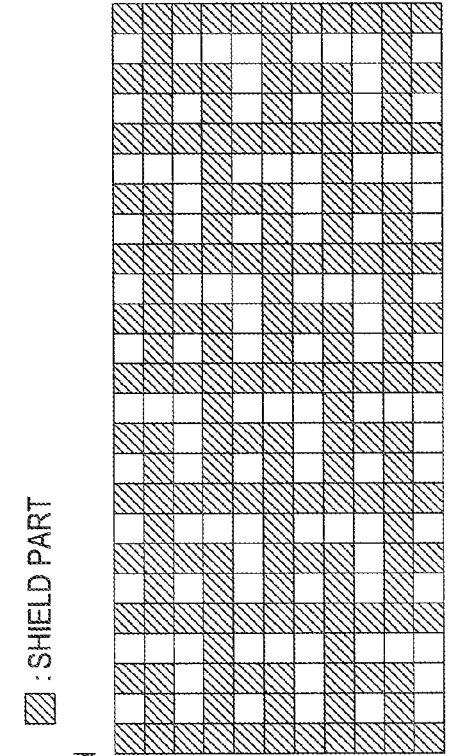

FIG. 9 is an illustration showing a first example of processing of the method of reducing the radiation exposure in accordance with the present embodiment. "A" shown in FIG. 9 shows one example of the first shield of the present embodiment, and "B" shown in FIG. 9 shows one example of the second shield of the present embodiment. "C1" shown in FIG. 9 shows a first example of a permeation aperture realized by the superposition of the first shield shown with "A" of FIG. 9 and of the second shield shown with "B" of FIG. 9, and "C2" shown in FIG. 9 shows a second example of a permeation aperture realized by the superposition of the first shield shown with "A" of FIG. 9 and of the second shield shown with "B" of FIG. 9.

For example, as shown in R1 of FIG. 9, the shape of the permeation aperture formed by the superposition becomes "the permeation apertures with the asymmetric shape prepared by combining the squares" as shown with A1 to A4 of FIG. 8 depending on the way of the superposition between the first shield and the second shield. For example, as shown in R2 of FIG. 9, the shape of the permeation aperture formed by the superposition becomes "the square-shaped permeation apertures" as shown at A5 of FIG. 8 depending on the way of the superposition between the first shield and the second shield.

Accordingly, for example, the X-rays can permeate the entire region "R" of the shield section 104 without any superposition of the permeating X-rays, for example, similar to B5 of FIG. 8 by appropriately using, for example, the permeation aperture shown with R1 of C1 of FIG. 9 and, for example, the permeation aperture shown with R2 of C2 of FIG. 9 at the respective stages in the time sharing, for example, as shown with A1 to A5 of FIG. 8.

It is needless to point out that the shapes of the first shield and the second shield of the present embodiment which can realize the shapes of the permeation apertures having "the permeation apertures with the asymmetric shape prepared by combining the squares" and "the square-shaped permeation apertures", respectively depending the way of the superposition between the first shield and the second shield of the present embodiment are not restricted to the shapes shown with "A" and "B" of FIG. 9.

[3-2] Second Example of Processing of Method of Reducing Radiation Exposure of Present Embodiment In the above first example of the processing of the method of reducing the radiation exposure of the present embodiment, the control of the positions of the shield section 104 through which the parallel X-ray beams permeate is exemplified by controlling the positions of "the permeation apertures with the asymmetric shape prepared by combining the squares" and "the square-shaped permeation apertures" by the X-ray output apparatus 100 at the respective stages. For example, this processing possesses an advantage that the shield is easily processed when the shapes of the permeation apertures of the shield section 104 are the squares or the asymmetric shape obtained by combining the squares. For example, this processing possesses an advantage that the relation with a lattice-shaped detector such as FPO included in the detection apparatus 200 can be easily created when the shapes of the permeation apertures of the shield section 104 are the squares or the asymmetric shape obtained by combining the squares. However, the processing of the method of reducing the radiation exposure of the present embodiment is not restricted to the processing of the above first example.

Figure 10:
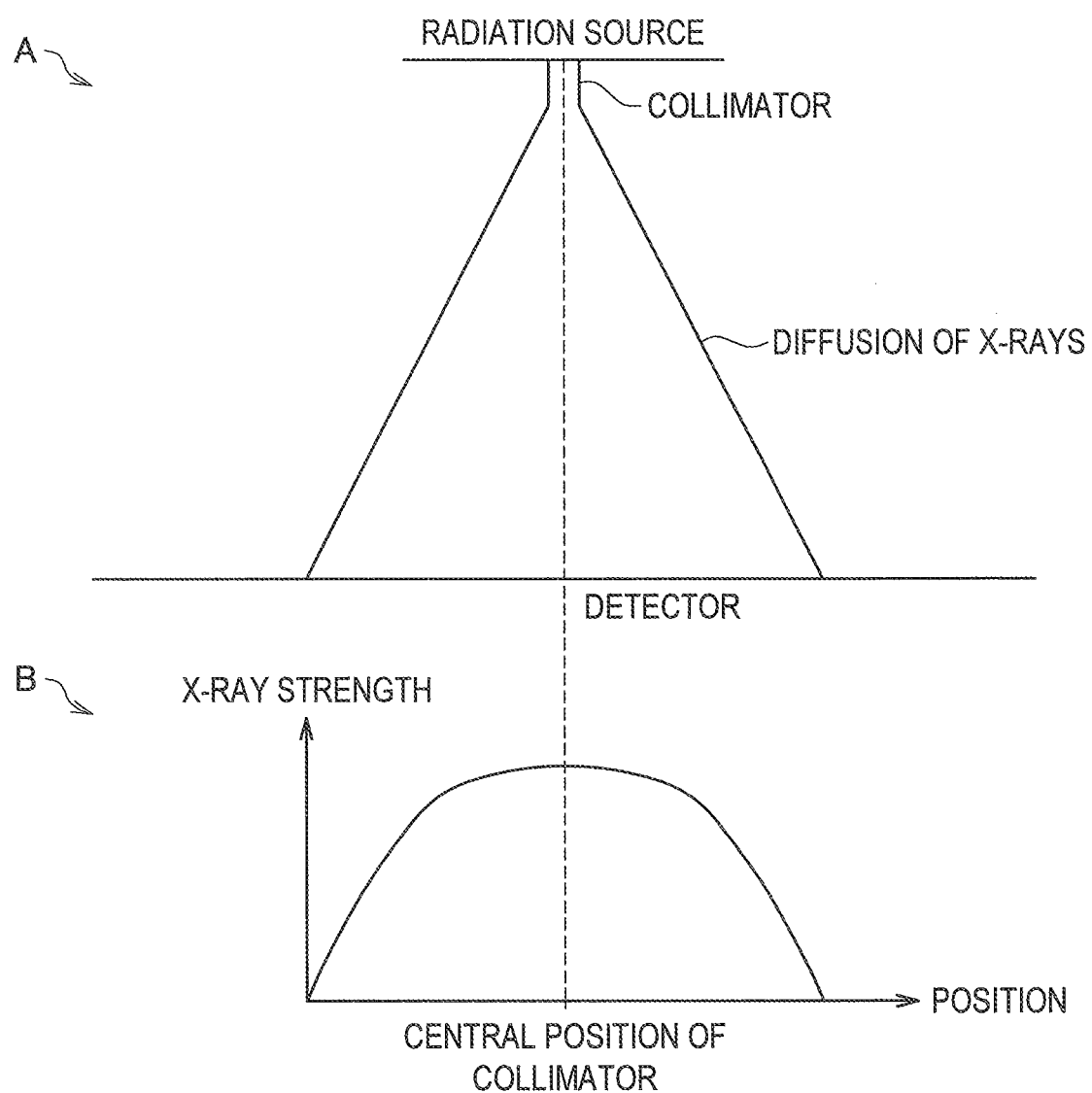
FIG. 10 is an illustration showing a second example of processing of a method of reducing radiation exposure in accordance with the present embodiment.

FIG. 10 is an illustration showing the second example of the processing of the method of reducing the radiation exposure of the present embodiment. FIG. 10 shows one example of diffusion of the parallel X-ray beams output via a collimator 112 in the X-ray output section 102, and one example of strength unevenness of the detected X-rays which may be produced by the X-ray diffusion.

As shown with "A" of FIG. 10, for example, even if the parallel X-ray beams are output via the collimator 112 in the X-ray output section 102, the X-ray diffusion occurs which possibly produces the strength unevenness in the X-rays detected by the detector of the detection apparatus 200.

Figure 11:
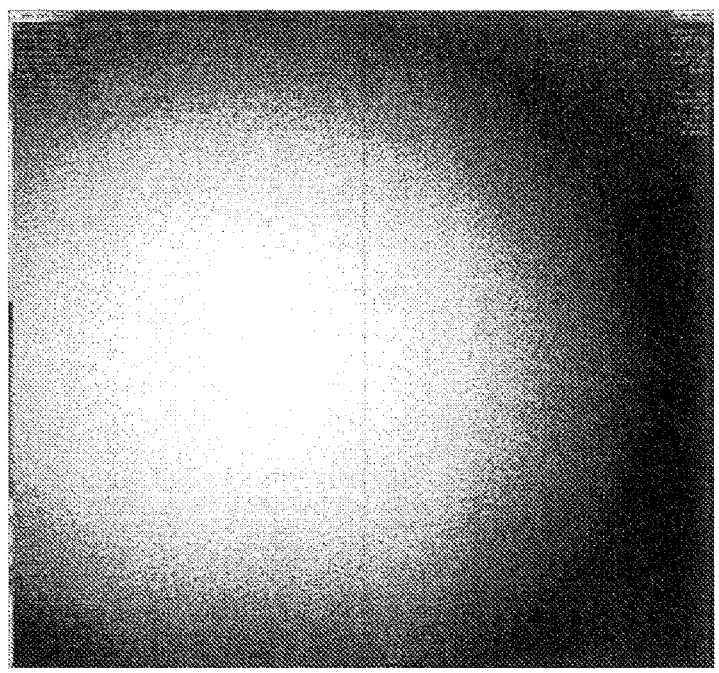
FIG. 11 is an illustration showing a second example of processing of a method of reducing radiation exposure in accordance with the present embodiment.
Figure 11:
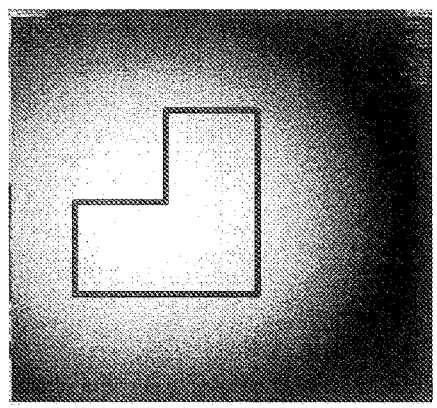
Figure 11:
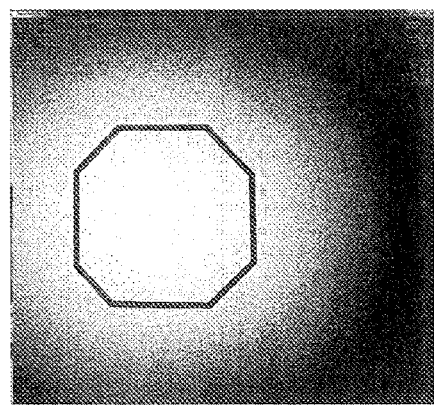

FIG. 11 is an illustration showing the second example of processing of the method of reducing the radiation exposure of the present embodiment. "A" shown in FIG. 11 shows one example of the strength unevenness of the X-rays detected by the detector of the detection apparatus 200. "A" shown in FIG. 11 shows one example of the strength unevenness of the X-rays detected by the detector of the detection apparatus 200 when the subject "O" does not exist. "B" shown in FIG. 11 shows one example of the shape of the permeation aperture in the shield section 104 in accordance with the above first example, and "C" shown in FIG. 11 shows one example of the shape of the permeation aperture in the shield section 104 in accordance with the above second example.

For example, in order to further reduce the influence of the strength unevenness of the X-rays as shown in FIG. 11, the shape of the permeation aperture in the shield section 104 is more advantageously a shape which is nearly a circle with a distance as small as possible from its center as shown with "C" of FIG. 11 than "the asymmetric shape prepared by combining the squares" of the above first example as shown with "B" of FIG. 11.

By making the permeation aperture in the shield section 104 to a nearly circular shape with the distance as small as possible from its center as shown at "C" of FIG. 11, the locality of the circumferential shape can be expected by using the distance from the central part. Accordingly, the X-ray images (entire image) corresponding to the subject can be constituted by using the X-ray images corresponding to the more stable X-ray-radiated parts, for example, in the image processing apparatus 300 by making the permeation aperture in the shield section 104 to the nearly circular shape with the distance as small as possible from its center as shown in "C" of FIG. 11.

Figure 12:
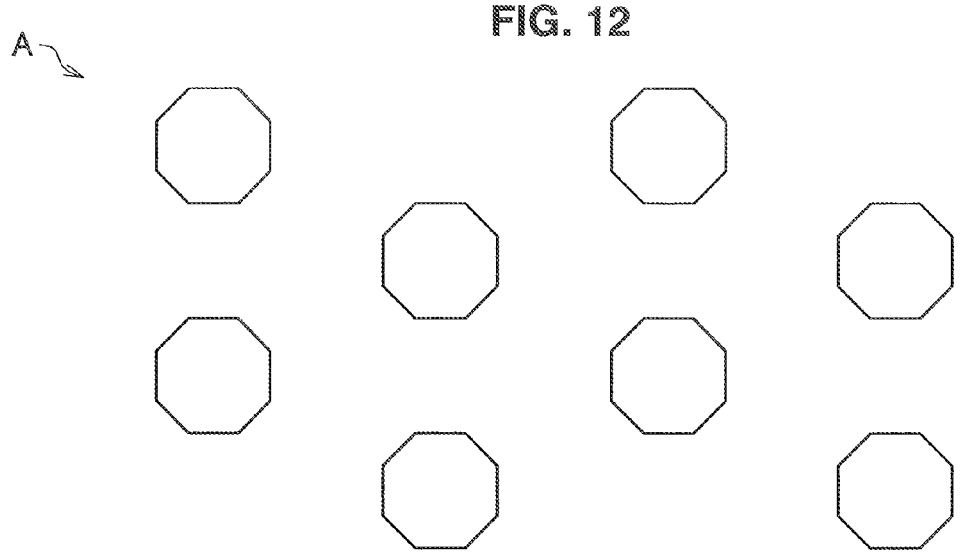
FIG. 12 is an illustration showing a second example of processing of a method of reducing radiation exposure in accordance with the present embodiment.
Figure 12:
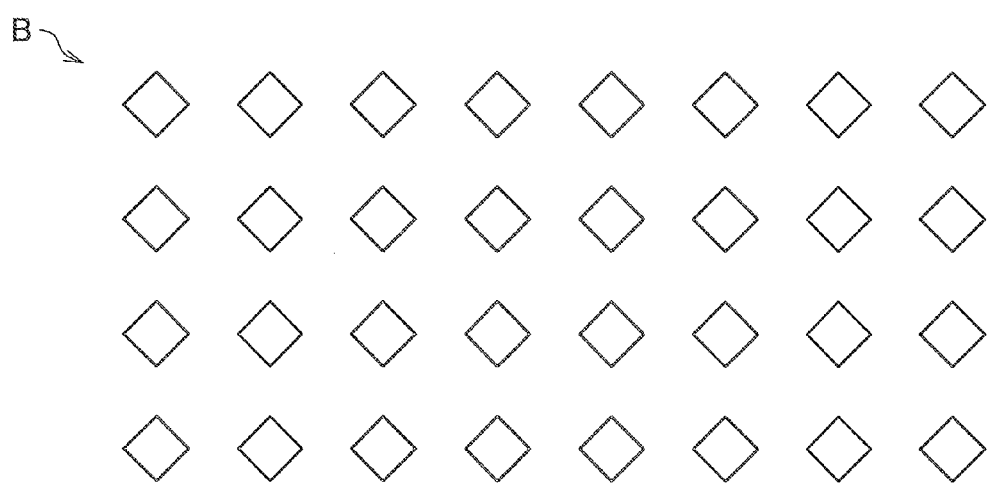
Figure 12:
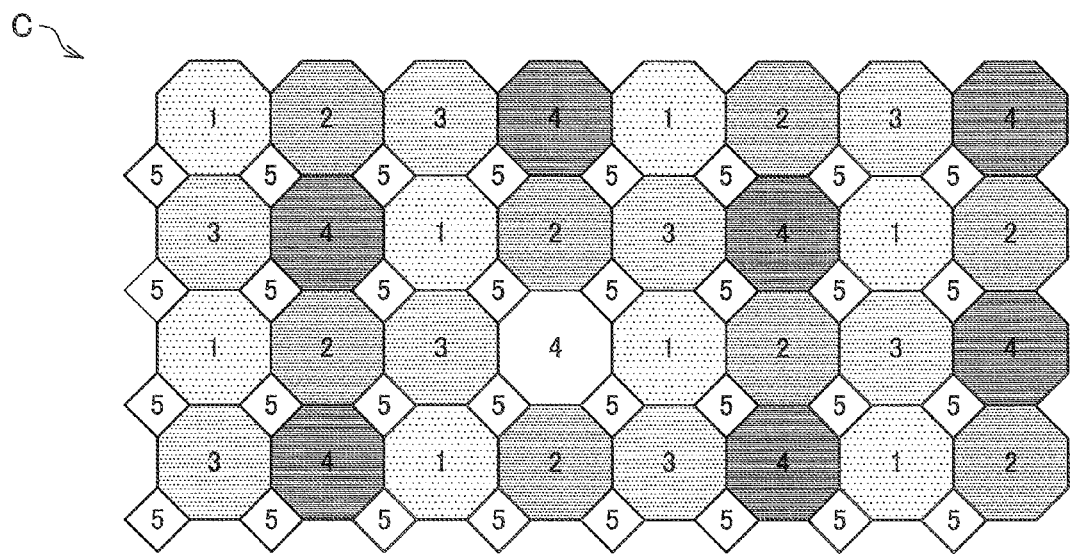

While the octagonal shape of the permeation aperture of the shield section 104 at "C" of FIG. 11 is exemplified, the shape of the permeation aperture (including a permeation aperture formed by the superposition of a plurality of the shields, hereinafter similarly applied) of the shield section 104 of the second example is not restricted to the octagon. For example, the shape of the permeation aperture of the shield section 104 of the second example may be various polygons such as a hexagon and a decagon which are nearer to a circle than a square. An example in which the shape of the permeation aperture of the shield section 104 of the second example is an octagon will be described, FIG. 12 is an illustration showing the second example of processing of the method of reducing the radiation exposure of the present embodiment. "A" shown in FIG. 12 shows one example of the second shield of the present embodiment, and "B" shown in FIG. 12 shows one example of the second shield of the present embodiment. "C1" shown in FIG. 12 shows one example of a permeation aperture realized by the superposition of the first shield shown with "A" of FIG. 12 and the second shield shown with "B" of FIG. 12.

"1" to "5" shown with "C" of FIG. 12 show one example of the positions through which the parallel X-ray beams permeate in a chronological order from "1" to "5". That is, FIG. 12 shows the example in which the positions in the shield section 104 through which the parallel X-ray beams permeate are controlled five times from "1" to "5" in the time sharing. As shown in the example shown in FIG. 12, the detection apparatus 200 detects the X-rays at the respective stages "1" to "5" of FIG. 12 when the positions in the shield section 104 through which the parallel X-ray beams permeate are controlled in the time-sharing manner.

"1" to "4" shown with "C" of FIG. 12 show one example in which the positions of the shield section 104 through which the parallel X-ray beams permeate are controlled by moving the first shield included in the shield section 104 to the positions shown by "1" to "4" shown with "C" of FIG. 12. "5" shown with "C" of FIG. 12 shows one example in which the positions of the shield section 104 through which the parallel X-ray beams permeate are controlled by moving the second shield included in the shield section 104 to the positions shown with "5" shown at "C" of FIG. 12.

The X-rays can permeate the entire region in the shield section 104 through which the parallel X-ray beams permeate without any superposition, for example, as shown with "C" of FIG. 12 by using "the octagonal permeation apertures" shown with "A" of FIG. 12 at the stages of "1" to "4" shown with the "C" of FIG. 12 and by using "the square permeation apertures" shown with "B" of FIG. 12 at the stage "5" shown with "C" of FIG. 12.

The X-ray images based on the parallel X-ray beams permeating the shield section 104 at the stage "5" shown with "C" of FIG. 12 are images having regions adjacent to each of the X-ray images based on the parallel X-ray beams permeating the shield section 104 at each of the stages "1" to "4" shown with "C" of FIG. 12. Accordingly, the X-ray images based on the parallel X-ray beams permeating the shield section 104 at the stage "5" shown with "C" of FIG. 12 can be a standard for correcting each of the X-ray images permeating the shield section 104 at the other stages (stages of "1" to "4" shown with "C" of FIG. 12). That is, the stage shown by "5" corresponds to the specified stage of the present embodiment among the respective stages in the time-sharing manner shown with "1" to "5" in "C" shown in FIG. 12, and the X-ray images based on the parallel X-ray beams permeating the shield section 104 at the stage "5" shown with "C" of FIG. 12 corresponds to the third X-ray images of the present embodiment.

The specified stage of the present embodiment is not restricted to the last stage in the time sharing such as the stage "5" shown with "C" in FIG. 12. For example, the X-ray output apparatus 100 can set any stage in the time sharing to the specified stage of the present embodiment by moving the shield included in the shield section 104, for example, by creating a situation similar to the stage "5" shown with "C" of FIG. 12.

The shapes of the permeation apertures at the specified stage (the stage "5" shown with "C" of FIG. 12 in the example of FIG. 12) among the shapes of the permeation apertures included in the shield section 104 through which the parallel X-ray beams permeate at the respective stages in the time sharing, for example, as shown in FIG. 12 are different from the shapes at the other stages (the stages "1" to "4" shown with "C" of FIG. 12 in the example of FIG. 12).

The X-ray output apparatus 100 controls the positions of the shield section 104 through which the parallel X-ray beams permeate, for example, at the respective stages "1" to "4" shown with "C" of FIG. 12 by using the first shield between the said first shield having "the octagonal permeation apertures" shown with "A" of FIG. 12 and the second shield having "the square-shaped permeation apertures" shown with "B" of FIG. 12. The X-ray output apparatus 100 controls the positions of the shield section 104 through which the parallel X-ray beams permeate, for example, at the stage "5" shown with "C" of FIG. 12 by using the second shield between the first shield having "the octagonal permeation apertures" shown with "A" of FIG. 12 and the said second shield having "the square-shaped permeation apertures" shown with "B" of FIG. 12.

The shapes of the permeation apertures included in the first shield of the present embodiment and those included in the second shield of the present embodiment are not restricted to "the octagon" as shown with "A" of FIG. 12 and to "the square" as shown with "B" of FIG. 12.

For example, the shapes of the permeation apertures included in the first shield and the second shield of the present embodiment may be such that the shape of a permeation aperture formed by the superposition of the first shield and the second shield of the present embodiment becomes "the octagon" or "the square" depending on a way of the superposition between the first shield and the second shield of the present embodiment.

Figure 13:
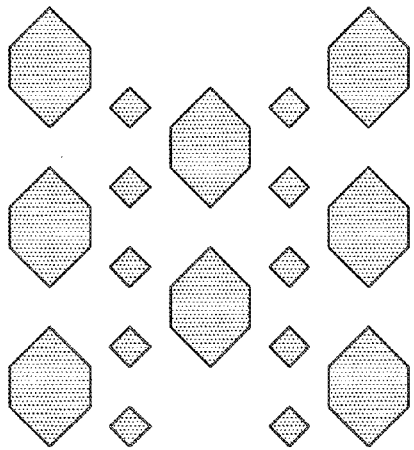
FIG. 13 is an illustration showing a second example of processing of a method of reducing radiation exposure in accordance with the present embodiment.
Figure 13:
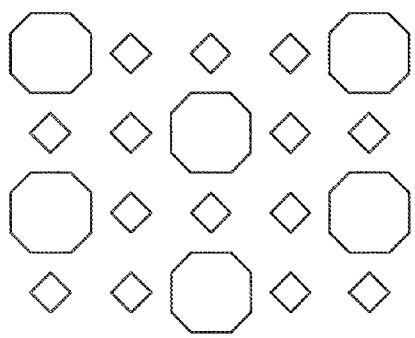
Figure 13:
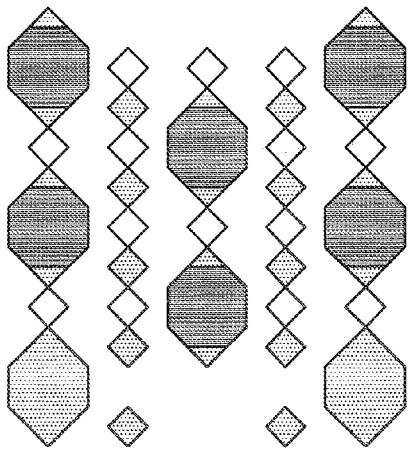
Figure 13:
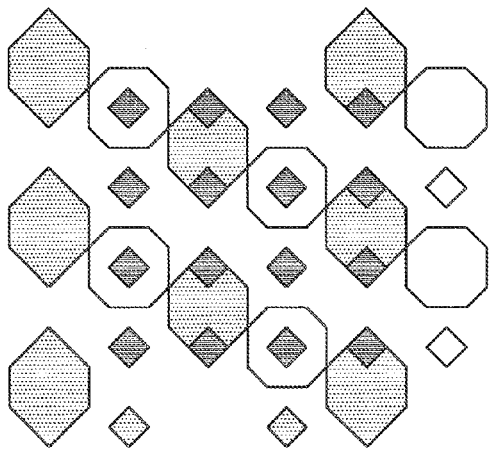

FIG. 13 is an illustration showing the second example of processing of the method of reducing the radiation exposure of the present embodiment. "A" shown in FIG. 13 shows one example of the first shield of the present embodiment, and "B" shown in FIG. 13 shows one example of the second shield of the present embodiment. "C1" shown in FIG. 13 shows one example of a permeation aperture realized by the superposition of the first shield shown with "A" of FIG. 13 and the second shield shown with "B" of FIG. 13, and "C2" shown in FIG. 13 shows a second example of a permeation aperture realized by the superposition of the first shield shown with "A" of FIG. 13 and the second shield shown with "B" of FIG. 13.

For example, as shown with "C1" of FIG. 13, the shapes of the permeation apertures formed by the superposition depending on a way of the superposition between the first shield and the second shield are the octagons as shown with "A" of FIG. 12. For example, as shown with "C2" of FIG. 13, the shapes of the permeation apertures formed by the superposition depending on a way of the superposition between the first shield and the second shield are the squares as shown with "B" of FIG. 12.

Accordingly, for example, the X-rays can permeate the entire region of the shield section 104 through which the parallel X-ray beams permeate without any superposition of the permeating X-rays, for example, similar to "C" of FIG. 12 by appropriately using, for example, the permeation aperture shown with C1 of FIG. 13 and, for example, the permeation aperture shown with C2 of FIG. 13 at the respective stages in the time sharing, for example, as shown with "1" to "5" of "C" of FIG. 12.

It is needless to point out that the shapes of the first shield and the second shield of the present embodiment which can realize the shapes of the permeation apertures having "the octagon" or "the square", respectively depending the way of the superposition between the first shield and the second shield of the present embodiment are not restricted to the shapes shown with "A" and "B" of FIG. 13.

(X-Ray Output Apparatus)

Then, one example of configuration of an X-ray output apparatus in accordance with the present embodiment will be described which can perform the processing of the method of reducing the radiation exposure of the present embodiment. One example of configuration of the X-ray output apparatus of the present embodiment will be described taking, as an example, a case in which the X-ray output apparatus of the present embodiment is the X-ray output apparatus 100 constituting the X-ray inspection system 100 shown in FIG. 1.

Figure 14:
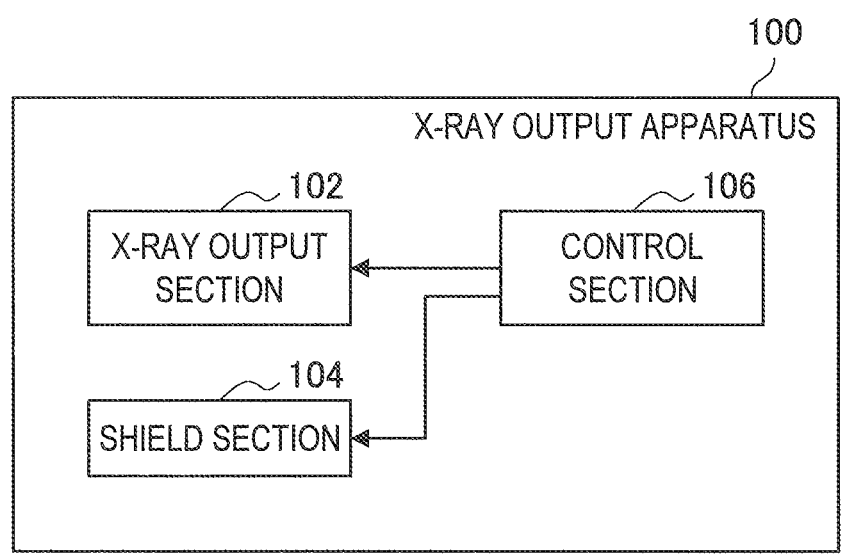
FIG. 14 is a block diagram showing one example of configuration of an X-ray output apparatus in accordance with the present embodiment.

FIG. 14 is a block diagram showing one example of configuration of the X-ray output apparatus 100 of the present embodiment. The X-ray output apparatus 100 includes, for example, an X-ray output section 102, a shield section 102 and a control section 106.

The X-ray output apparatus 100 may include, for example, ROM (not shown) and RAM (not shown) and a communication section (not shown). For example, the X-ray output apparatus 100 connects the above constituents through a bus acting as a transmission channel of data.

The ROM (not shown) stores control data such as a program used in the control section 106 and an operation parameter. The RAM (not shown) temporarily stores a program implemented by the control section 106.

The communication section (not shown) is a communication means included in the X-ray output apparatus 100, and has a role of performing the communication by wired or wireless with an external device such as an image processing apparatus 300.

The communication section (not shown) includes, for example, a communication antenna and an RF circuit (wireless communication), an IEEE 802.15.1 port and a transmitting and receiving circuit (wireless communication), and an IFFF802.11b port and a transmitting and receiving circuit (wireless communication), or a LAN terminal and a transmitting and receiving circuit (wired communication). The communication section (not shown) includes, for example, a configuration corresponding to any standard capable of performing the communication such as a USB terminal and a transmitting and receiving circuit, and any configuration communicable with an external device via a network.

[Configuration Example of Hardware of X-Ray Output Apparatus 100]

Figure 15:
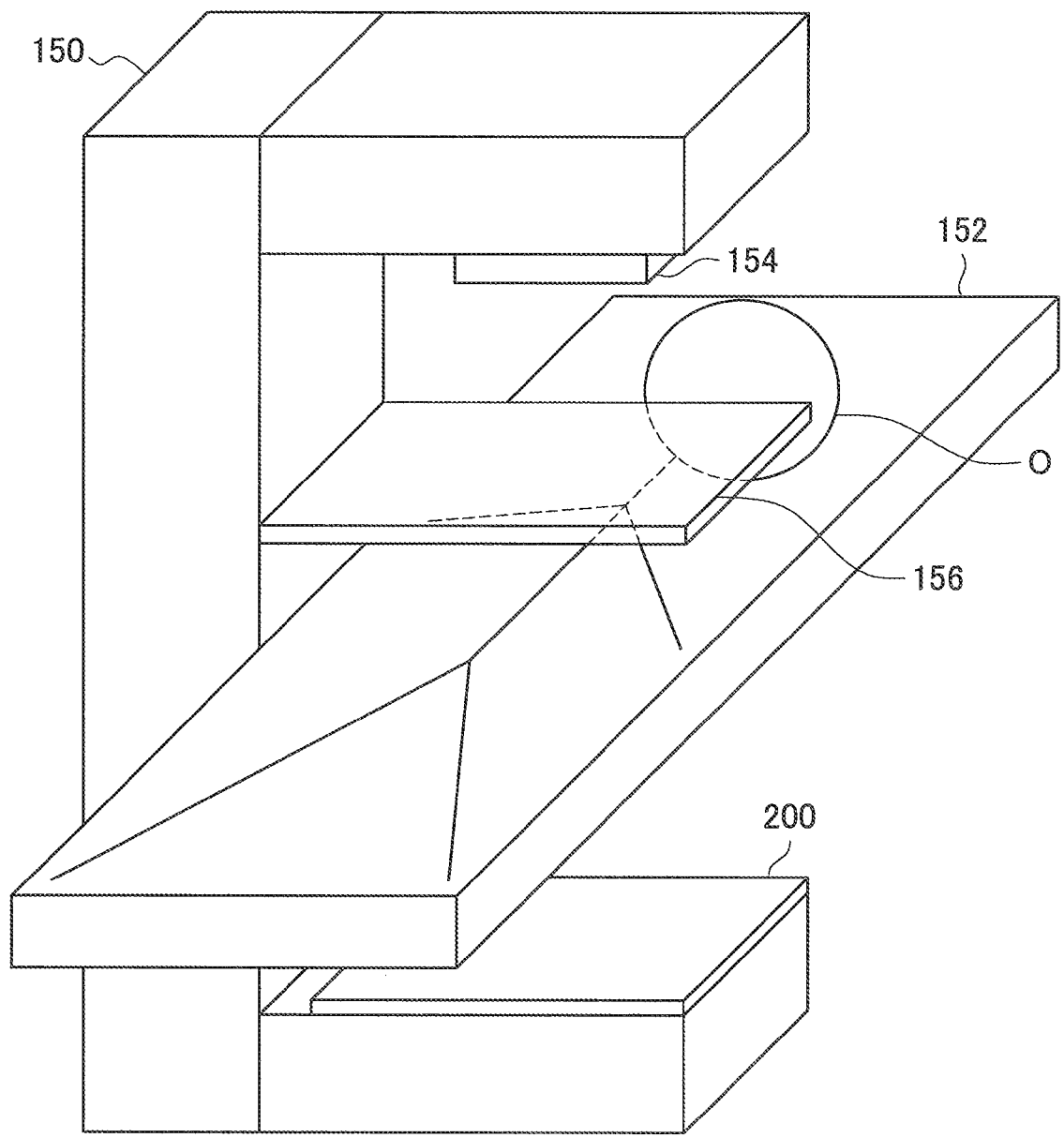
FIG. 15 is an illustration showing one example of configuration of hardware of an X-ray output apparatus in accordance with the present embodiment.

FIG. 15 is an illustration showing one example of configuration of hardware of the X-ray output apparatus 100 of the present embodiment. FIG. 15 additionally shows one example of the detection apparatus 200 such as FPD. FIG. 15 shows a human as one example of the subject "O".

The X-ray output apparatus 100 includes, for example, an arm 150 holding each of the constituents, a radiographic stand 152, a multipoint parallel X-ray source 154 and a shield 156. Although not shown in FIG. 15, the X-ray output apparatus 100 includes, for example, MPU (not shown) and various processing circuits acting as the control section 106 initiatively performing the processing of the method of reducing the radiation exposure of the above present embodiment at the interior of the arm 150. Further, the X-ray output apparatus 100 includes a drive device for moving, for example, the shield 156.

The arm 150 holds the various constituents of the X-ray output apparatus 100, and the detection apparatus 200. The radiographic stand 152 holds the subject "O".

The multipoint parallel X-ray source 154 includes, for example, a plurality of X-ray tubes and a plurality of collimators for outputting the parallel X-ray beams, and acts as the X-ray output section. The multipoint parallel X-ray source 154 generates the X-rays by the X-ray tubes, forms the parallel X-ray beams by the above X-rays together with X-rays generated by the collimators, and outputs the parallel X-ray beams toward a bottom direction shown in FIG. 15.

The shield 156 is formed by a metal which can block the X-rays such as lead and iron, and acts as the shield section 104. For example, as shown in FIG. 15, the shield 156 having a role as the shield section 104 is mounted facing the output direction of the parallel X-ray beams at the multipoint parallel X-ray source 154 having a role as the X-ray output section 102, and mounted between the multipoint parallel X-ray source 154 having a role as the X-ray output section 102 and the subject "O" to which the X-rays are radiated.

The X-ray output apparatus 100, for example by means of the configuration shown in FIG. 15, performs the processing of the method of reducing the radiation exposure of the present embodiment. The hardware configuration of the X-ray output apparatus 100 according to an embodiment of the present disclosure is not restricted to the configuration shown in FIG. 15.

For example, while the configuration including one shield 156 is shown in FIG. 15, the X-ray output apparatus 100 of the present embodiment may be the configuration including the plurality of the shields as described above.

While the X-ray output apparatus 100 and the detection apparatus 200 are described to be separate devices, for example, in the above description, the X-ray output apparatus 100 and the detection apparatus 200 may be a unit device. When the X-ray output apparatus 100 and the detection apparatus 200 are the unit device, the detection apparatus 200 acts as, for example, a detecting section for detecting the parallel X-ray beams output from the X-ray output section 102.

The X-ray output apparatus 100 may further include, for example, a communication device for conducting communication with an external device such as the image processing apparatus of the present embodiment by wired or wireless. The above communication device has a role of a communication section (not shown) in the X-ray output apparatus 100. The communication section (not shown) included in the X-ray output apparatus 100 includes, for example, a communication antenna and an RF circuit (wireless communication), an IEEE 802.15.1 port and a transmitting and receiving circuit (wireless communication), and an IFFF802.11b port and a transmitting and receiving circuit (wireless communication), or a LAN terminal and a transmitting and receiving circuit (wired communication). The communication device included in the X-ray output apparatus 100 is a device corresponding to any standard capable of performing the communication such as a USB terminal and a transmitting and receiving circuit, and any device communicable with an external device via a network.

One example of the configuration of the X-ray output apparatus 100 will be again described referring to FIG. 14. As described above, the X-ray output section 102 includes the plurality of the X-ray sources 110 for outputting the parallel X-ray beams.

More specifically, the X-rays are generated in the X-ray source 110 by bombarding an anode target of the X-ray tube with electrons by means of flowing current through a cathode filament of the X-ray tube constituting the X-ray source 110 of the X-ray output section 102, for example, in response to signals transmitted from the control section 106. The collimator 112 of the X-ray output section 102 converts the generated X-rays into the parallel X-ray beams.

The shield section 104 blocks the output parallel X-ray beams. The shield section 194 includes the permeation apertures for permeating the parallel X-ray beams as shown in FIG. 8, FIG. 9, FIG. 12 and FIG. 13, and includes the shield for blocking the parallel X-ray beams by the part other than the permeation apertures. The position through which the parallel X-ray beams can permeate is variable in the shield section 104, for example, by changing the position of the permeation aperture by the movement of the shield. The movement of the shield included in the shield section 104 is conducted in the time-sharing manner, for example, as shown with A1 to A5 of FIG. 8 and "1" to "5" of "C" of FIG. 12, and the movement of the shield included in the shield section 104 is controlled by the control section 106.

The control section 106 has a role of initiatively performing the processing of the method of reducing the radiation exposure of the present embodiment, and controls the output of the parallel X-ray beams at the X-ray output section 102 and the position through which the parallel X-ray beams permeate. The control section 106 is configured, for example, by MPU and various processing circuits.

The control section 106 controls the position of the shield section 104 through which the parallel X-ray beams permeate in the time-sharing manner, for example, by moving one or more shields included in the shield section 104. More specifically, the control section 106 performs, for example, the processing of the method of reducing the radiation exposure of the present embodiment in accordance with the first example as shown with A1 to A5 of FIG. 8, and the processing of the method of reducing the radiation exposure of the present embodiment in accordance with the second example as shown with "C" of FIG. 12, and controls the position of the shield section 104 through which the parallel X-ray beams permeate in the time-sharing manner.

The movement of the shield included in the shield section 104 is conduced, for example, by a drive device included in the X-ray output apparatus 100. For example, the drive device may be a device configuring the control section 106 or another device different from the control section 106. The control section 106 controls the position of the shield section 104 through which the parallel X-ray beams permeate in the time-sharing manner by transmitting control signals for controlling the drive and by moving the one or more shields included in the shield section 104 in the time-sharing manner, for example, to the above drive device.

The control section 106 stops, for example, the output of the parallel X-ray beams at the X-ray output section 104 when the shield included in the shield section 104 is moved Then, control section 106 outputs the parallel X-ray beams to the X-ray output section 102 after the movement of the shield included in the shield section 104 is completed.

While the control section 106 controls the outputs of the parallel X-ray beams from each of the plurality of the X-ray sources 110 included in the X-ray output section 102 in a synchronizing manner, the control of the X-ray output section 102 at the control section is not restricted to the above. For example, the control section 106 may output the parallel X-ray beams to the X-ray output section 10-2 only to a position corresponding to a position of the shield section 104 through which the parallel X-ray beams permeate when the parallel X-ray beams are output to the X-ray output 102 by individually controlling each of the plurality of the X-ray sources 110 included in the X-ray output 102.

The processing at the control section 106 is not restricted to the above.

For example, the control section 106 may make a device which displays the images based on the X-ray detection data of the parallel X-ray beams having permeated the shield section 104 perform the display corresponding to the control of the output of the parallel X-ray beams at the X-ray output section 102 and of the position of the shield section through which the parallel X-ray beams permeate (the display corresponding to the processing of the method of reducing the radiation exposure of the present embodiment). One example in which the device of displaying the images based on the X-ray detection data of the parallel X-ray beams having permeated the shield section 104 is the image processing apparatus 300 will be hereinafter described.

More specifically, the control section 106 makes a communication section (not shown) included in the X-ray output apparatus 100 or an externally communication device transmit, for example, display processing information to the image processing apparatus 300. The display processing information of the present embodiment includes, for example, information (data) controlling the display corresponding to the respective stages in the time sharing.

The display processing information of the present embodiment includes, for example, information showing the respective stages in the time-sharing. The display method of the present embodiment includes, for example, "a display method in which assigned color is mixed in each of regions corresponding to the respective stages in the time sharing for display" and "a display method in which each of regions corresponding to the respective stages in the time sharing is displayed every stage of the time sharing".

The image processing apparatus 300 receiving the display control information of the present embodiment displays, on a display surface, the display corresponding to "the output of the parallel X-ray beams at the X-ray output apparatus, and the control of the position through which the parallel X-ray beams permeate" based on the X-ray detection data (or projection data) transmitted from the detection apparatus 200 and the display control information.

By means of transmitting the display control information of the present embodiment from the X-ray output apparatus 100 to the image processing apparatus 300, the image control device 300 displays, on the display surface, the X-ray images corresponding to the subject, by using the display method of the present embodiment such as "the display method in which the assigned color is mixed in each of the regions corresponding to the respective stages in the time sharing. A user who watches the X-ray images corresponding to the subject displayed on the display surface by using the display method according to an embodiment of the present disclosure can more easily understand, for example, that how many images the user has watched before watching this X-ray image in the time-sharing manner, and that whether or not this X-ray image is already stitched. The user who watches the X-ray images corresponding to the subject displayed on the display surface by the display method according to an embodiment of the present embodiment can easily perform the processing, for example, when the modification processing for the better superposing is conducted.

Accordingly, the X-ray output apparatus 100 can elevate the user friendliness by making the image processing apparatus 300 conduct the display corresponding to the control of the X-ray output of the parallel X-ray beams and the position through which the parallel X-ray beams permeate.

The X-ray output apparatus 100, for example by means of the configuration shown in FIG. 14, controls the output of the parallel X-ray beams at the X-ray output section 102 and the position of the shield section 104 through which the parallel X0ray beans permeate, and conducts the processing of the method of reducing the radiation exposure of the present embodiment, The shield section 104 includes the permeation apertures through which the parallel X-ray beams permeate and includes the shield for blocking the parallel X-ray beams in the part other than the permeation apertures, and the X-ray output apparatus 100 controls the position of the shield section through which the parallel X-ray beams permeate.

Accordingly, the X-ray output apparatus 100 decreases, for example, the invalid radiation exposure as shown in R1 to R4 of FIG. 6, and can reduce the superfluous radiation exposure given to the subject.

When the X-ray output apparatus 100 performs the processing of the method of reducing the radiation exposure of the present embodiment, the image processing apparatus 300 corrects each of the plurality of the fourth X-ray images using the third X-ray images of the present embodiment as a standard similarly to the case in which the plurality of the first X-ray images are corrected by using the second X-ray image as a standard, and superposes the third X-ray images of the present embodiment and the corrected plurality of fourth X-ray images of the present embodiment. Accordingly, when the X-ray output apparatus 100 performs the processing of the method of reducing the radiation exposure of the present embodiment, the image processing apparatus 300 can obtain the X-ray images corresponding to the subject of the higher quality images and undistinguished seams, for example, similarly to the case of which the processing is described referring to FIG. 5.

When the X-ray output apparatus 100 performs the processing of the method of reducing the radiation exposure of the present embodiment, the X-ray images (the third X-ray images of the present embodiment and the fourth X-ray images of the present embodiment) corresponding to each of the detection results detected in the time-sharing manner include no regions overlapping with the other X-ray images. Accordingly, when the X-ray output apparatus 100 performs the processing of the method of reducing the radiation exposure of the present embodiment, an amount of the radiation exposure to the subject can be reduced more than the case in which each of the plurality of the first X-ray images is corrected using the second X-ray images as a standard, for example, as shown with reference to FIG. 4.

Accordingly, by performing the processing of the method of reducing the radiation exposure of the present embodiment by the X-ray output apparatus 100, the X-ray images of high quality can be obtained which correspond to the subject obtained by the superposition of the X-ray images corresponding to each of the detection results detected in the time-sharing manner while the superfluous radiation exposure to the subject is reduced.

When the X-ray output apparatus 100 performs the processing of the method of reducing the radiation exposure of the present embodiment, the image processing apparatus 300 superposes, for example, each of the third X-ray images of the present embodiment and each of the plurality of the corrected fourth X-ray images of the present embodiment. Accordingly, when the X-ray output apparatus 100 performs the processing of the method of reducing the radiation exposure of the present embodiment, the image processing apparatus 300 can produce the X-ray images having, for example, the higher quality and the undistinguished seams corresponding to the subject by conducting a relatively simple adding calculation without a blending calculation of the complicated X-ray images.

Accordingly, when the X-ray output apparatus 100 performs the processing of the method of reducing the radiation exposure of the present embodiment, the real-time tendency of the processing at the image processing apparatus 300 can be further elevated, and an amount of calculation memory necessary for the processing by the image processing apparatus 300 can be reduced.

The configuration of the X-ray output apparatus of the present embodiment is not restricted to the configuration shown in FIG. 14.

For example, the X-ray output apparatus of the present embodiment may further include a detection section (not shown) including similar functions and configuration as those of the detector shown in FIG. 1. The X-ray output apparatus of the present embodiment may further include a detection section (not shown) including similar functions and configuration as those of the detector shown in FIG. 1.

The X-ray output apparatus of the present embodiment is not configured by one device all the time. For example, the X-ray output apparatus of the present embodiment may be an X-ray output system configured by a plurality of devices such as "a system configured by the control section 106, the X-ray output section and/or the shield section 104 each of which is a separate device". When the X-ray output apparatus of the present embodiment is configured by the plurality of the devices, the device having a role as the control section 106 initiatively performs the processing of the method of reducing the radiation exposure of the present embodiment for controlling the device having a role as the X-ray output apparatus and the device having a role as the shield section, thereby realizing the X-ray output system which can reduce the superfluous radiation exposure to the subject.

While the X-ray output apparatus has been described as one example of the present embodiment, the present embodiment shall not be restricted thereto. The present embodiment can be applied to various devices such as a CT (Computed Tomography) device (a device using omnidirectional projection data), an X-ray imaging device such as mammography and a device having a tomosynthesis function (a device using the projection data in a limited angle direction, for example, less than 180 degree C.).

(Program of Present Embodiment)

A program for driving a computer as the X-ray output apparatus of the present embodiment (a program for implementing the processing of the method of reducing the radiation exposure of the present embodiment such as, for example, a program for functioning as the control section 106 shown in FIG. 14) is implemented in the computer so as to control the output of the parallel X-ray beams at the X-ray output section, and the position of the shield section through which the parallel X-ray beams permeate so that the superfluous radiation exposure to the subject can be reduced. A program for driving a computer as the X-ray output apparatus of the present embodiment is implemented in the computer so as to control the output of the parallel X-ray beams at the X-ray output section, and the position of the shield section through which the parallel X-ray beams permeate so that the high quality X-ray images corresponding to the subject obtained by the superposition of the X-ray images corresponding to each of the detection results detected in the time-sharing manner. The above X-ray output section and the shield section may be, for example, devices included in the computer, or may be external devices of the computer.

At first, a program for driving a computer as the X-ray output apparatus of the present embodiment (a program for implementing "the processing for conducting the display corresponding to the control of the output of the parallel X-ray beams and of the position through which the parallel X-ray beams permeate, to a device for displaying images based on the X-ray detection data of the parallel X-ray beams having permeated the shield section", for example, at the control section 106 shown in FIG. 14) is implemented in the computer so as to increase the user's convenience.

It should be understood by those skilled in the art that various modifications, combinations, sub-combinations and alterations may occur depending on design requirements and other factors insofar as they are within the scope of the appended claims or the equivalents thereof.

While, for example, the program (computer program) for acting the computer as the X-ray output apparatus of the present embodiment has been provided, a storage medium which stores the above program can also be provided.

The above configurations show examples of the embodiments, and naturally belong to the technical scope of the present disclosure, Additionally, the present technology may also be configured as below.

(1) An X-ray output apparatus including:

an X-ray output section including a plurality of X-ray sources and outputting parallel X-ray beams;

a shield section capable of changing a position which blocks the output parallel X-ray beams and permeate the parallel X-rays beams; and a control section controlling an output of the parallel X-ray beams at the X-ray output section and the position which permeates the parallel X-ray beams at a shield section, wherein the shield section includes a permeation aperture through which the parallel X-ray beams permeate, and a shield which blocks the parallel X-ray beams at a portion other than the permeation aperture, wherein the control section controls, in a time-sharing manner, a position through which the parallel X-ray beams permeate in the shield section by moving the shield included in the shield section, wherein a shape of the permeation aperture at a specified stage among shapes of the permeation aperture included in the shield section which permeates the parallel X-ray beams among respective stages of the time sharing is different from a shape of another stage, and wherein the control section controls the position of the shield section at permeates the parallel X-ray beams are permeated such that an X-ray image based on each of the parallel X-ray beams at the respective stages in the time sharing manner which permeate the shield section includes no region overlapping with the other X-ray images.

(2) The X-ray output apparatus according to (1),
wherein the X-ray images based on the parallel X-ray beams and permeating the shield section at the specified stage is a standard of correcting each of the X-ray images permeating the shield section at another stage.

(3) The X-ray output apparatus according to (1) or (2),
wherein the shield section includes a plurality of shields each having a permeation aperture in which shapes of the permeation apertures of the respective shields are different from one another, and
wherein the control section controls, at the respective stages where the position of the shield section through which the parallel X-ray beams permeate is controlled in a time-sharing manner, the position through which the parallel X-ray beams are permeated at the shield section by using the plurality of the shields among the plurality of the shields included in the shield.

(4) The X-ray output apparatus according to (1) or (2),
wherein the shield section includes a plurality of the shields each having an permeation aperture in which shapes of the permeation apertures of the respective shields are different from one another, and
wherein the control section controls, at the respective stages where the position of the shield section through which the parallel X-ray beams permeate is controlled in a time-sharing manner, the position through which the parallel X-ray beams are permeated at the shield section by using one of the shields among the plurality of the shields included in the shield.

(5) The X-ray output apparatus according to any one of (1) to (4),
wherein the shield section includes
a first shield including the permeation aperture, and
a second shield including the permeation aperture of which a shape is different from the shape of the permeation aperture of the first shield.

(6) The X-ray output apparatus according to (5),
wherein the shape of the permeation aperture of the first shield is an asymmetric shape obtained by combining squares, and
wherein the shape of the permeation aperture of the second shield is a square.

(7) The X-ray output apparatus according to (5),
wherein the shape of the permeation aperture of the first shield and the shape of the permeation aperture of the second shield are set in a manner that when the first shield and the second shield are superposed, the shape of the permeation aperture thus formed is an asymmetric shape formed by combination of squares or a square depending on a way of superposition between the first shield and the second shied.

(8) The X-ray output apparatus according to (5),
wherein the shape of the permeation aperture of the first shield is a polygon which is nearer to a circle than to a square, and
wherein the shape of the permeation aperture of the second shield is a square.

(9) The X-ray output apparatus according to (8),
wherein the shape of the permeation aperture of the first shield is an octagon.

(10) The X-ray output apparatus according to (5),
wherein the shape of the permeation aperture of the first shield and the shape of the permeation aperture of the second shield are set in a manner that when the first shield and the second shield are superposed, the shape of the permeation aperture thus formed is a polygon which is nearer to a circle than to a square or a square, depending on a way of superposition between the first shield and the second shied.

(11) The X-ray output apparatus according to (1) or (2),
wherein the shield section includes one shield including a plurality of permeation apertures.

(12) The X-ray output apparatus according to any one of (1) to (11),
wherein, when the shield included in the shield section is moved, the control section stops output of the parallel X-ray beams at the X-ray output section, and
wherein, after completion of movement of the shield, the control section causes the X-ray output section to output the parallel X-ray beams.

(13) The X-ray output apparatus according to (12),
wherein the control section causes the X-ray output section to output the parallel X-ray beams only to a position corresponding to a position of the shield section through which the parallel X-ray beams are permeated.

(14) The X-ray output apparatus according to any one of (1) to (13),
wherein the shield section is mounted facing an output direction of the parallel X-ray beams at the X-ray output section, and mounted between the X-ray output section and the subject onto which the X-ray beams are emitted.

What is claimed is:

1. An X-ray output apparatus comprising:
an X-ray output section including a plurality of X-ray sources and outputting parallel X-ray beams;
a shield section capable of changing a position which blocks the output parallel X-ray beams and permeate the parallel X-rays beams; and
a control section controlling an output of the parallel X-ray beams at the X-ray output section and the position which permeates the parallel X-ray beams at a shield section,
wherein the shield section includes a permeation aperture through which the parallel X-ray beams permeate, and a shield which blocks the parallel X-ray beams at a portion other than the permeation aperture,
wherein the control section controls, in a time-sharing manner, a position through which the parallel X-ray beams permeate in the shield section by moving the shield included in the shield section,
wherein a shape of the permeation aperture at a specified stage among shapes of the permeation aperture included in the shield section which permeates the parallel X-ray beams among respective stages of the time sharing is different from a shape of another stage, and
wherein the control section controls the position of the shield section at permeates the parallel X-ray beams are permeated such that an X-ray image based on each of the parallel X-ray beams at the respective stages in the time sharing manner which permeate the shield section includes no region overlapping with the other X-ray images.

2. The X-ray output apparatus according to claim 1,
wherein the X-ray images based on the parallel X-ray beams and permeating the shield section at the specified stage is a standard of correcting each of the X-ray images permeating the shield section at another stage.

3. The X-ray output apparatus according to claim 1,
wherein the shield section includes a plurality of shields each having a permeation aperture in which shapes of the permeation apertures of the respective shields are different from one another, and wherein the control section controls, at the respective stages where the position of the shield section through which the parallel X-ray beams permeate is controlled in a time-sharing manner, the position through which the parallel X-ray beams are permeated at the shield section by using the plurality of the shields among the plurality of the shields included in the shield.

4. The X-ray output apparatus according to claim 1, wherein the shield section includes a plurality of the shields each having an permeation aperture in which shapes of the permeation apertures of the respective shields are different from one another, and wherein the control section controls, at the respective stages where the position of the shield section through which the parallel X-ray beams permeate is controlled in a time-sharing manner, the position through which the parallel X-ray beams are permeated at the shield section by using one of the shields among the plurality of the shields included in the shield.

5. The X-ray output apparatus according to claim 1, wherein the shield section includes
a first shield including the permeation aperture, and
a second shield including the permeation aperture of which a shape is different from the shape of the permeation aperture of the first shield.

6. The X-ray output apparatus according to claim 5, wherein the shape of the permeation aperture of the first shield is an asymmetric shape obtained by combining squares, and wherein the shape of the permeation aperture of the second shield is a square.

7. The X-ray output apparatus according to claim 5, wherein the shape of the permeation aperture of the first shield and the shape of the permeation aperture of the second shield are set in a manner that when the first shield and the second shield are superposed, the shape of the permeation aperture thus formed is an asymmetric shape formed by combination of squares or a square depending on a way of superposition between the first shield and the second shied.

8. The X-ray output apparatus according to claim 5, wherein the shape of the permeation aperture of the first shield is a polygon which is nearer to a circle than to a square, and wherein the shape of the permeation aperture of the second shield is a square.

9. The X-ray output apparatus according to claim 8, wherein the shape of the permeation aperture of the first shield is an octagon.

10. The X-ray output apparatus according to claim 5, wherein the shape of the permeation aperture of the first shield and the shape of the permeation aperture of the second shield are set in a manner that when the first shield and the second shield are superposed, the shape of the permeation aperture thus formed is a polygon which is nearer to a circle than to a square or a square, depending on a way of superposition between the first shield and the second shied.

11. The X-ray output apparatus according to claim 1, wherein the shield section includes one shield including a plurality of permeation apertures.

12. The X-ray output apparatus according to claim 1, wherein, when the shield included in the shield section is moved, the control section stops output of the parallel X-ray beams at the X-ray output section, and wherein, after completion of movement of the shield, the control section causes the X-ray output section to output the parallel X-ray beams.

13. The X-ray output apparatus according to claim 12, wherein the control section causes the X-ray output section to output the parallel X-ray beams only to a position corresponding to a position of the shield section through which the parallel X-ray beams are permeated.

14. The X-ray output apparatus according to claim 1, wherein the shield section is mounted facing an output direction of the parallel X-ray beams at the X-ray output section, and mounted between the X-ray output section and the subject onto which the X-ray beams are emitted.

* * * * *